US012776427B2

(12) United States Patent
Alizadeh-Meghrazi et al.

(10) Patent No.: US 12,776,427 B2
(45) Date of Patent: Oct. 27, 2026

(54) APPARATUS AND METHOD OF MANUFACTURING OF CONDUCTIVE THERMOPLASTIC ELASTOMER ELECTRODES

(71) Applicant: MGI HOLDCO LTD., Toronto (CA)

(72) Inventors: Milad Alizadeh-Meghrazi, Toronto (CA); Ladan Eskandarian, Toronto (CA); Amin Mahnam, Toronto (CA); Bastien Moineau, Toronto (CA); Sahar Golmhammadi Rostami, Toronto (CA); Christopher Robin Leiphart, Toronto (CA); Andrea Ferrone, Toronto (CA); Shayan Niakan, Toronto (CA)

( * ) Notice: Subject to any disclaimer, the term of this patent is extended or adjusted under 35 U.S.C. 154(b) by 273 days.

(21) Appl. No.: 18/138,499

(22) Filed: Apr. 24, 2023

(65) Prior Publication Data

US 2023/0343482 A1 Oct. 26, 2023

Related U.S. Application Data

(60) Provisional application No. 63/333,651, filed on Apr. 22, 2022.

(51) Int. Cl.

| | |
|---|---|
| ***H01B 5/14*** | (2006.01) |
| ***A61B 5/27*** | (2021.01) |
| ***A61N 1/04*** | (2006.01) |
| ***H01B 1/02*** | (2006.01) |
| ***H01B 1/12*** | (2006.01) |

(52) U.S. Cl.

CPC ................. *H01B 5/14* (2013.01); *A61B 5/27* (2021.01); *A61N 1/0484* (2013.01); *H01B 1/02* (2013.01); *H01B 1/124* (2013.01); *A61B 2562/0215* (2017.08)

(58) Field of Classification Search

CPC ......... H01B 5/14; H05K 1/0243; H05K 1/023

USPC .......................................................... 174/260

See application file for complete search history.

(56) References Cited

U.S. PATENT DOCUMENTS

| | | | | |
|---|---|---|---|---|
| 2011/0147673 A1* | 6/2011 | Gaillard | D01F 1/09 252/514 |
| 2018/0108542 A1* | 4/2018 | Pagaila | H01L 24/81 |
| 2022/0189666 A1* | 6/2022 | Crevenat | H05K 1/181 |
| 2023/0328886 A1* | 10/2023 | Shin | H05K 1/185 174/260 |
| 2023/0345616 A1* | 10/2023 | Micovic | H05K 1/023 |
| 2024/0196529 A1* | 6/2024 | Berzowska | A61B 5/257 |

FOREIGN PATENT DOCUMENTS

WO WO 2022/060166 * 3/2022

* cited by examiner

*Primary Examiner* — Chau N Nguyen
(74) *Attorney, Agent, or Firm* — Dickinson Wright LLP

(57) ABSTRACT

An apparatus and method of manufacturing same is provided. The apparatus includes: a base layer integrated with an article; a conductive layer in communication with a base contact pad mounted on the base layer; an active electrode board in electrical communication with the base contact pad, the active electrode board configured to receive or send electrical signals from the base contact pad; and a contact layer in electrical communication with the conductive layer, and the conductive layer is mounted on the base layer; wherein the active electrode board comprises a board contact pad configured to receive or send electrical signals from the base contact pad.

12 Claims, 28 Drawing Sheets

APPARATUS AND METHOD OF MANUFACTURING OF CONDUCTIVE THERMOPLASTIC ELASTOMER ELECTRODES

CROSS-REFERENCE TO RELATED APPLICATION

This application claims the benefit of and priority to U.S. provisional patent application No. 63/333,651 filed on Apr. 22, 2022, the entire content of which is herein incorporated by reference.

FIELD

This relates to textile based electrodes, and in particular to electrodes formed of conductive thermoplastic elastomers.

BACKGROUND

Electrodes may be used for sensing biopotential signals or imparting electrical stimulation to a person's body. Wet gel has been used in electrodes to reduce impedance at the skin-electrode interface to improve sensing of biopotential signals or the ability to impart electrical energy to a person's body. However, application of a wet gel to a person's body may be difficult or undesirable for certain applications.

SUMMARY

In one aspect, the disclosure describes apparatus having: a base layer integrated with an article; a conductive layer in communication with a base contact pad mounted on the base layer; an active electrode board in electrical communication with the base contact pad, the active electrode board configured to receive or send electrical signals from the base contact pad; and a contact layer in electrical communication with the conductive layer, and the conductive layer is mounted on the base layer; wherein the active electrode board comprises a board contact pad configured to receive or send electrical signals from the base contact pad.

In some embodiments, the base contact pad may include a base contact surface configured to be in communication with a board contact surface of the board contact pad, and the base contact surface and the board contact surface have corresponding surface size.

In some embodiments, the base contact surface and the board contact surface have corresponding surface shape.

In some embodiments, the contact layer may include yarn having a conductive filler, In some embodiments, the conductive layer may include silver yarn.

In some embodiments, the base contact pad may include conductive knitted yarn.

In some embodiments, the conductive knitted yarn may include copper microwire,

In some embodiments, the base contact surface and the board contact surface are configured to be connected using a solder paste.

In some embodiments, the solder paste is applied at a low temperature within a range of 130 to 170 degrees Celsius.

In some embodiments, the apparatus may include a coating on the active electrode board.

In some embodiments, the coating exposes a board contact surface of the board contact pad for connecting to the base contact pad.

In some embodiments, the coated active electrode board is attached to the base layer using a laminate material.

In some embodiments, the laminate material and the base layer are bounded using heat activated glue.

In some embodiments, the laminate material may include thermoplastic polyurethane (TPU).

In some embodiments, the contact layer may include an electrode configured to convert ionic current at a skin-electrode interface to electrical signals when the electrode is coupled to a user.

In some embodiments, the active electrode board and the base layer are mechanically fused together using ultrasonic welding.

In some embodiments, the article is an article of clothing.

In another aspect, the disclosure describes a method of manufacturing an article, the method comprising: providing a base layer integrated with an article; providing an active electrode board having a board contact pad; coating the active electrode board with a conformal coating material, wherein the coating exposes a surface of the board contact pad; positioning the coated active electrode board to the base layer, wherein the board contact pad of the coated active electrode board aligns with a base contact pad of the base layer, attaching the board contact pad to the base contact pad using solder paste; and attaching the coated active electrode board to the base layer using a laminate material.

In some embodiments, the base contact pad may include conductive knitted yarn.

In some embodiments, the conductive knitted yarn may include copper microwire.

In some embodiments, the laminate material and the base layer are bounded using heat activated glue.

In some embodiments, the laminate material may include thermoplastic polyurethane (TPU).

In some embodiments, the base layer is integrated with a contact layer, and the contact layer comprises yarn having a conductive filler.

In some embodiments, the contact layer is in electrical communication with a conductive layer mounted on the base layer.

In some embodiments, the conductive layer may include silver yarn.

In some embodiments, the method includes mechanically fusing the active electrode board and the base layer using ultrasonic welding.

In yet another aspect, the disclosure describes an electrode comprising a contact layer comprising a filament, the filament comprising a thermoplastic elastomer.

In an embodiment, the contact layer comprises a conductive filler blended with the thermoplastic elastomer. The contact layer may comprise a second filament comprising a conductive or nonconductive filament.

In an embodiment, the contact layer comprises yarn comprising the first filament.

In an embodiment, the contact layer is backed with a layer of conductive yarn. The conductive yarn may be silver yarn.

Embodiments may include combinations of the above features.

In still another aspect, the disclosure describes an apparatus comprising a base layer integrated with an article; an electrode mounted adjacent to a conductive layer, both the electrode and conductive layer mounted on the base layer; an active electrode board in electrical communication with the conductive layer and the electrode, the active electrode board configured receive and/or send electrical signals from the electrode; wherein the electrode comprises filaments or filament yarn, the filaments or filament yarn knitted into a textile, the filaments or filament yarn comprising thermoplastic elastomers (TPE) blended with one or more conductive fillers.

In an embodiment, the apparatus comprises a first overmould of the active electrode board. The apparatus may also comprise a shield mounted over or inside the overmould of the active electrode board. The apparatus may comprise a second overmould over the first overmould and the shield, the second overmould connecting to the base layer.

In an embodiment, the electrode is configured to convert ionic current at a skin-electrode interface to electrical signals when the electrode is coupled to a user. The active electrode board may comprise a preamplifier for increasing signal strength from the electrode when the electrode is coupled to a user.

In an embodiment, the electrode is configured to apply electrical current to a user.

In an embodiment, the article is an article of clothing.

In another aspect, the disclosure describes a method of manufacturing a filament for an electrode, the method comprising: providing TPE polymer pellets having desired material properties; combining polymer pellets and conductive filler together to form a conductive TPE; extruding and drawing the conductive TPE into a filament; optionally, forming yarn from the filament; and knitting the yarn and/or filament into an electrode.

In an embodiment, the TPE polymer and conductive filler are comprise biocompatible material for forming a biocompatible yarn and/or filament.

Embodiments may include combinations of the above features.

Further details of these and other aspects of the subject matter of this application will be apparent from the detailed description included below and the drawings.

DESCRIPTION OF THE DRAWINGS

Reference is now made to the accompanying drawings, in which.

DETAILED DESCRIPTION

Figure 1:
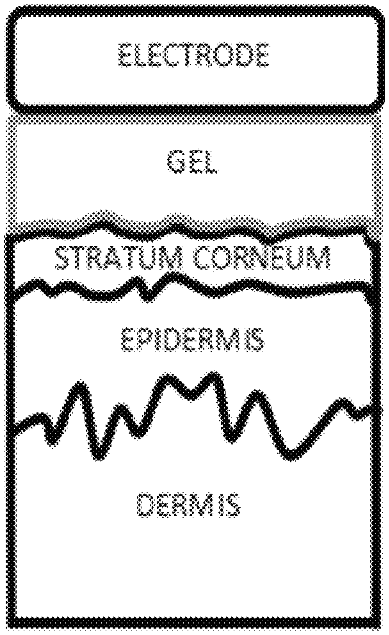
FIG. 1 (Prior Art)
FIG. 1 is a prior art example of an electrode-gel-skin interface.

The following description relates to a textile-based electrode formed from thermoplastic elastomer material, suitable for sensing biopotential signals including Electromyogram (EMG), Electroencephalogram (EEG), Electrocardiogram (ECG), Electrooculogram (EOG), and Electrogastrogram (EGG), as well as applying current/voltage to body for Functional Electrical Stimulation (FES), Transcranial Current Stimulation (TCS), High-Frequency Alternating Current Stimulation, and/or creating a tactile sensation. The description also describes method(s) of manufacturing the thermoplastic elastomer yarns, electrode (s), and apparatus disclosed herein.

The term "substantially" as used herein may be applied to modify any quantitative representation which could permissibly vary without resulting in a change in the basic function to which it is related. The term "proximate" as used herein may refer to the direction or surface that is closest to a contact point between an electrode and skin of a user. The term "flat form factor" as used herein may refer to an electrode wherein a proximate surface of conductive filament or filament yarn is in the same plane material adjacent to the electrode. The term "raised form factor" as used herein may refer to an electrode wherein a proximate surface of conductive filament or filament yarn is in a plane the above material surrounding and adjacent to the electrode.

An electrode acts as a transducer in converting the ionic current in/on the body into electron currents in conductive wires and electronic circuits, and vice versa. Various activities in the body can be measured, such as heart activity with electrocardiography (ECG), muscle activity with electromyography (EMG), brain activity with electroencephalography (EEG), and eye movements with electrooculography (EOG). The electrode-skin interface is the interface that performs this transduction between the electrode and skin while they are in contact. Electrode-skin impedance at the electrode-skin interface may dictate how well the signal will be transduced, and consequently, the signal quality.

A skin's outer layer is the epidermis, consisting of sublayers including the outermost Stratum Corneum. The Stratum Corneum is made of dead keratin-filled corneocytes arranged in a brick-and-mortar pattern. Lipid lamellae exist between the corneocytes, through which conductive ions need to pass in order to travel from the deeper layer of skin to the electrodes during bipotential measurements. When temperature and humidity increase in the Stratum Corneum, the fluidity of these lipids increases, allowing water and small molecules to move through the lipid lamellae more easily. Thus, hydrating the Stratum Corneum allows for higher signal quality in biopotential measurement.

An electrode may generally be defined as conductive material through which electricity passes to a body of a user and/or is received from the body of a user. A sensor is a subset of electrodes which receives electrical energy for measurement/recordation. In an embodiment, electrode 100 may be used as a sensor. In another embodiment, electrode 100 may be an actuator to inject electrical current/voltage to the body, e.g. for FES to inject electrical pulses to activate muscles.

Standard electrodes may use an electrolytic gel to maintain good electrical contact with the Stratum Corneum, creating an ionic path between the electrode and the skin below the Stratum Corneum via conductive ions in the gel. This reduces the skin impedance and allows for improved signal acquisition. The skin-electrode interface for wet electrodes is shown in FIG. 1. However, the standard wet gel electrode used currently, e.g. in healthcare, may have limitations. The adhesive can cause skin irritation and becomes uncomfortable over time, the gel dehydrates with time thus degrading signal quality, and the electrode can be uncomfortable to the user, due to its metallic piece, therefore a soft, textile form is an inconspicuous alternative for continuous health monitoring.

Figure 2:
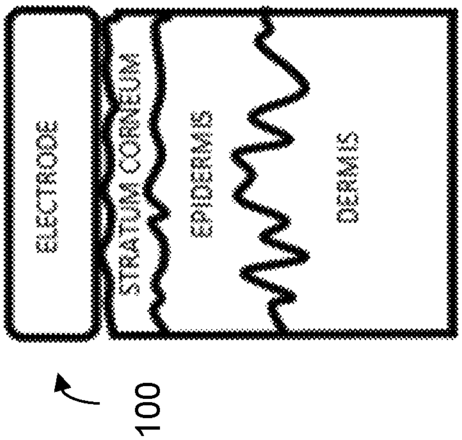
FIG. 2 is an example electrode-skin interface according to the present disclosure.

Dry contact electrodes can be categorized according to form factor into textile electrodes, flexible film electrodes, bulk electrodes, pin-shaped electrodes, and microneedles. An example skin-electrode interface for dry electrodes is depicted in FIG. 2, differing in that it does not contain the gel layer. Dry electrodes may be biocompatible, easy to use, comfortable, breathable, lightweight, flexible, washable, durable, and able to maintain good signal quality during electrophysiology testing while at rest and moving. Additionally, textile-based electrodes may be worn on various body parts by attaching them to, or integrating them into, different articles of clothing such as waistbands, sleeves, pants, and headbands.

Figure 3:
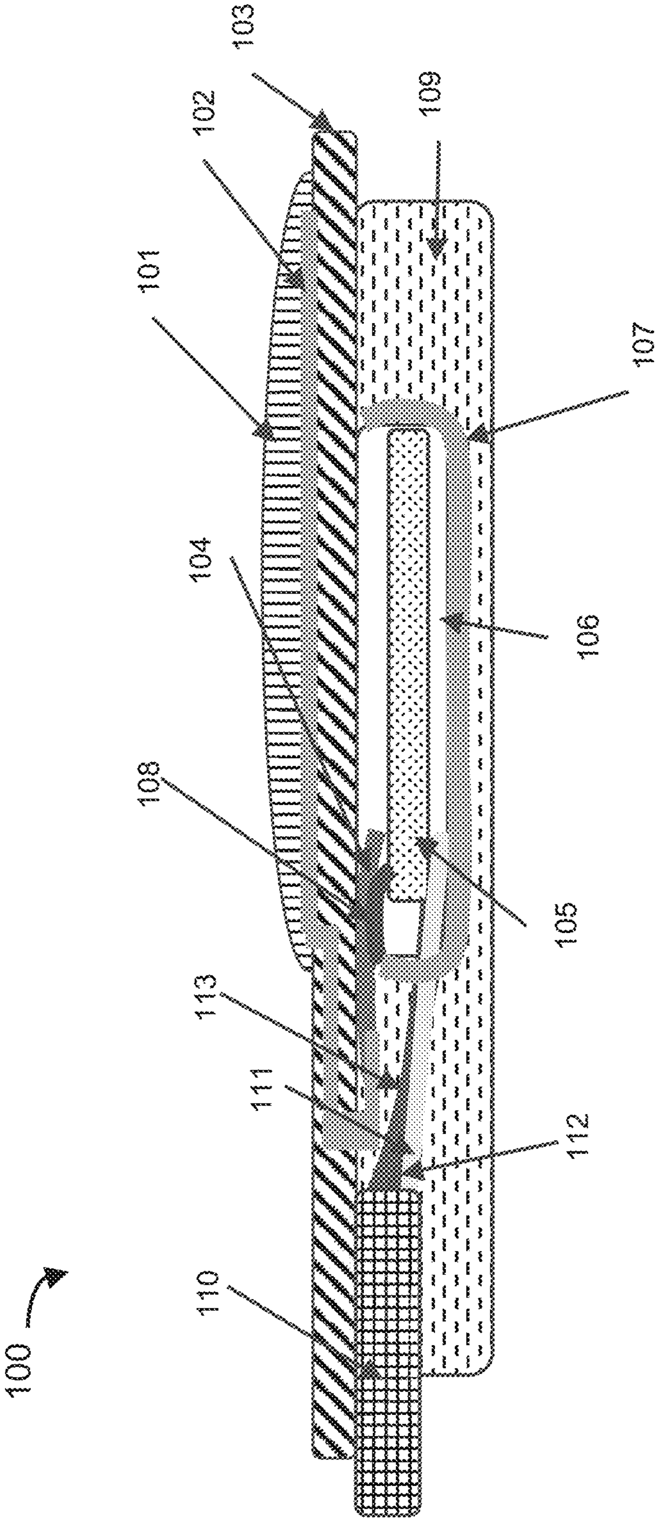
FIG. 3 is a side cross-sectional view of an example apparatus according to the present disclosure.
Figure 4B:
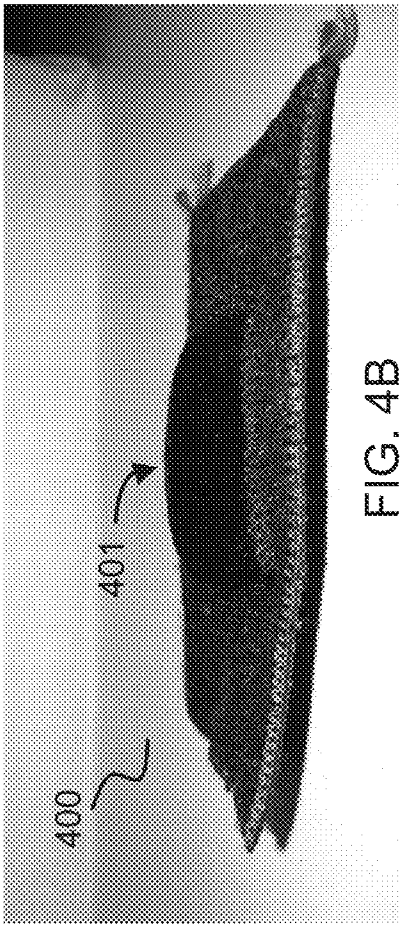
FIGS. 4B and 4C each illustrates a side perspective view of the example electrode of FIG. 4A showing the raised form factor.
Figure 4C:
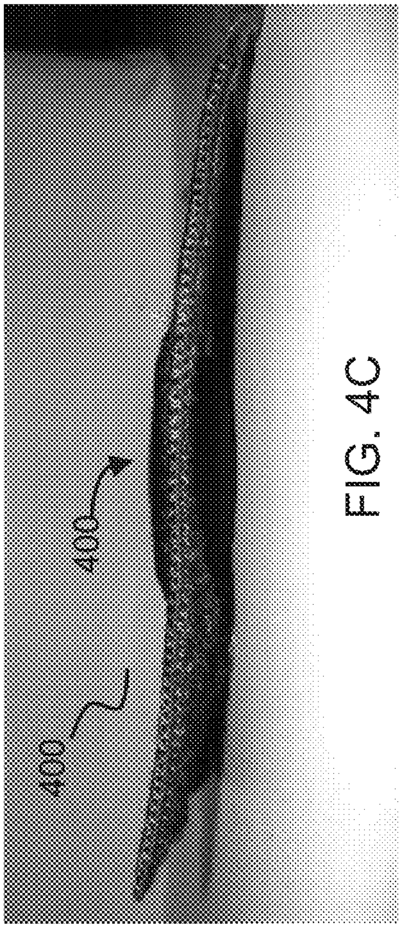
Figure 4A:
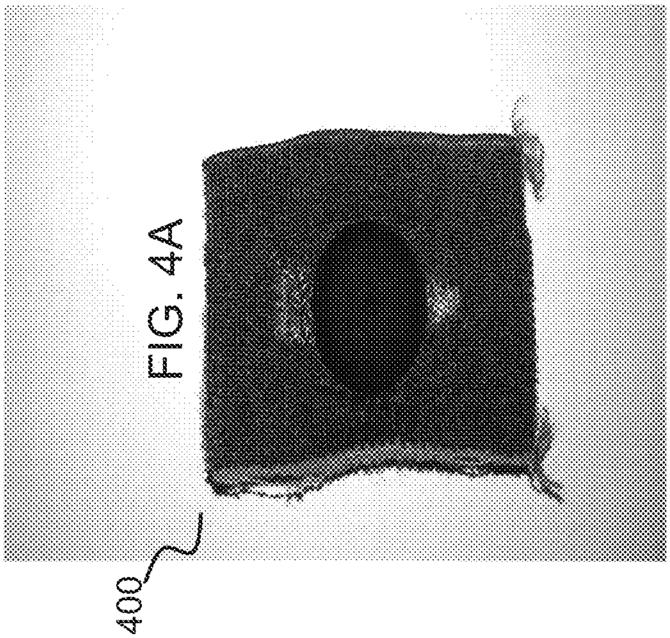
FIG. 4A is an overhead view of an example electrode having a raised form factor.

An example developed electrode is illustrated in FIG. 4A-C. The example electrode 400 of FIGS. 4A-C has a raised form factor F (FIG. 3): a circular 2-cm diameter electrode that is knit using conductive Thermoplastic Elastomer filament connected to a more conductive layer on its back. The conductive back layer may be silver-plated nylon, polyester, Kevlar yarn, stainless steel and/or metallic microwire wrapped around polyester, nylon, viscose, rayon, and/or aramid yarn. Conductive layer may be defined beneath contact layer. Contact layer and conductive layer may be mounted on a base layer or be part of an article. In an embodiment, base layer may be a non-conductive double layer fabric. As shown in FIGS. 3, contact layer may have a raised form factor such that contact layer defines a surface in a plane above (i.e. more proximate to a user than) base layer. A raised form factor may promote sustained contact between contact layer and a user. Base layer may be part of an article, e.g. clothing or furniture, having a surface area.

FIGS. 4B and 4C illustrate a side perspective view of the example electrode showing raised form factor 401. Raised form factor 401 may promote sustained contact a surface-to-skin interface between a user and a contact layer of the raised form factor 401.

A plurality of electrodes according to the present disclosure may be part of a garment, and each of the plurality of electrodes may be integral to an article (e.g. clothing) forming a uniform structure.

Figure 5:
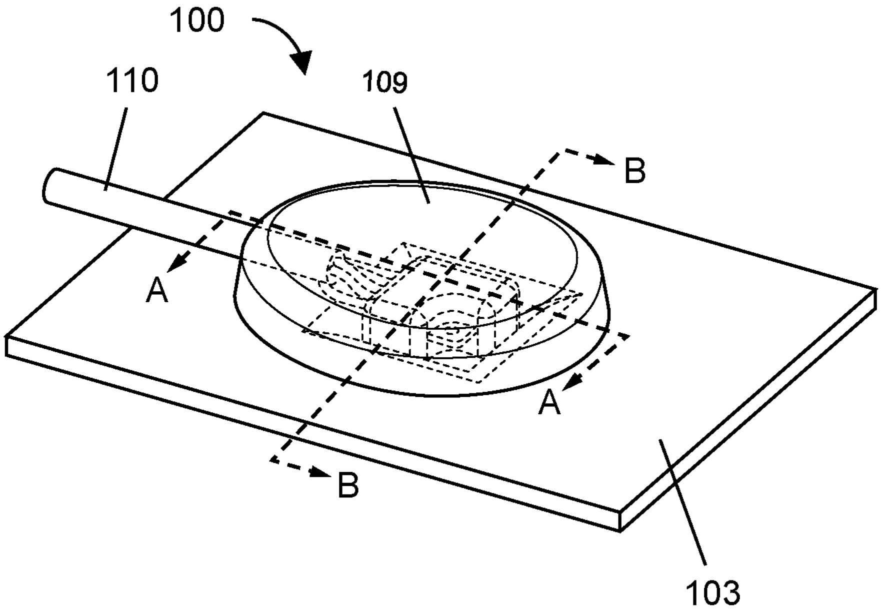
FIG. 5 is a perspective view of an apparatus according to the present disclosure comprising an overmoulded active electrode board.
Figure 6:
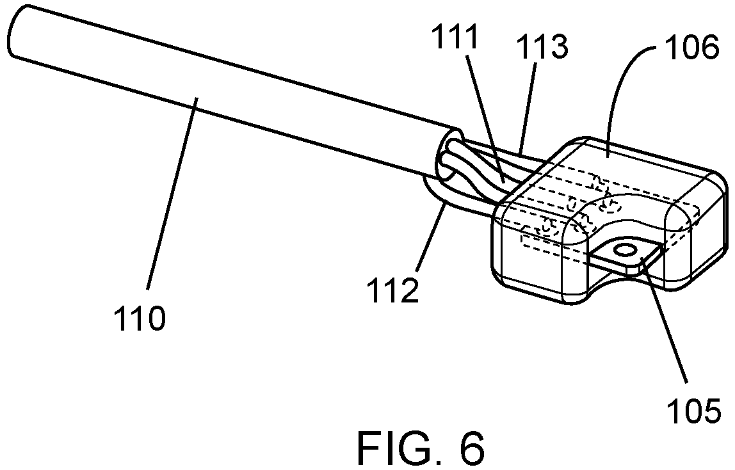
FIG. 6 is a perspective view of the overmoulded active electrode board of FIG. 5.

An example apparatus 100 according to the disclosure herein is illustrated in FIGS. 3 and 5. Apparatus 100 is a dry electrode comprising Thermoplastic Elastomers (TPE) combined with conductive material. For example, the conductive material may be a conductive filler (i.e. conductive dopant) or a conductive coating. As illustrated in FIG. 3, contact layer 101 comprises conductive TPE yarn comprising a TPE combined with conductive filler. In another embodiment, contact layer 101 may comprise conductive material coated onto a TPE. Contact layer 101 is in electrical communication with conductive layer 102. In an embodiment, conductive layer 102 may be silver-plated nylon, polyester, Kevlar yarn and/or silver-plated copper microwire wrapped around polyester or nylon yarn 102. Conductive layer 102 may be defined beneath contact layer 101. Contact layer 101 and conductive layer 102 may be mounted on base layer 103 as shown in FIG. 3. In an embodiment, base layer 103 may be a non-conductive double layer fabric. As shown in FIGS. 3, 7A, 78, and 8 contact layer 101 may have a raised form factor such that contact layer 101 defines a surface in a plane above (i.e. more proximate to a user than) base layer 103. A raised form factor may promote sustained contact between contact layer 101 and a user. Base layer 103 may be part of an article, e.g. clothing or furniture, having a surface area. In an embodiment, the article may comprise a plurality of apparatus 100 which may be integral with the article.

Figure 7A:
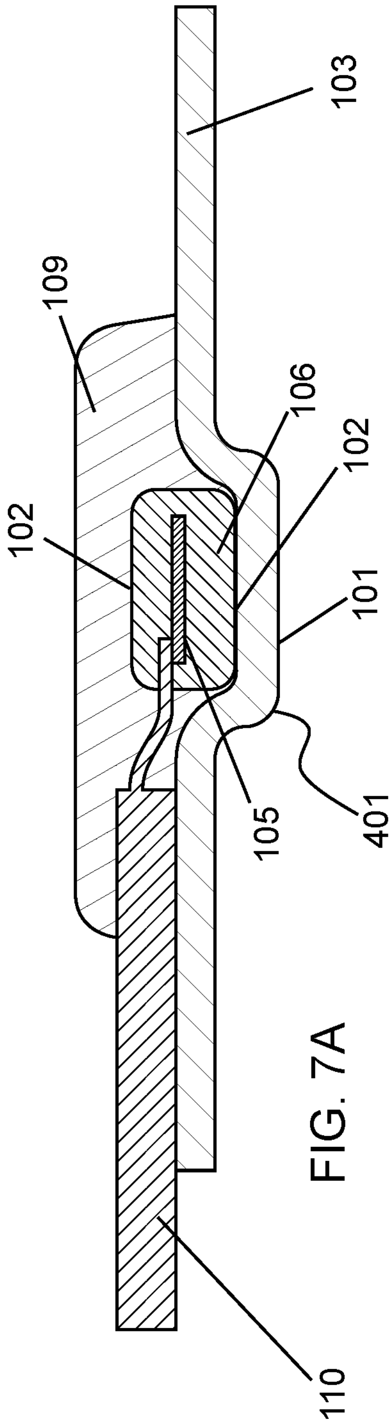
FIG. 7A is a cross sectional view of the apparatus of FIG. 5 along the line A-A.
Figure 7B:
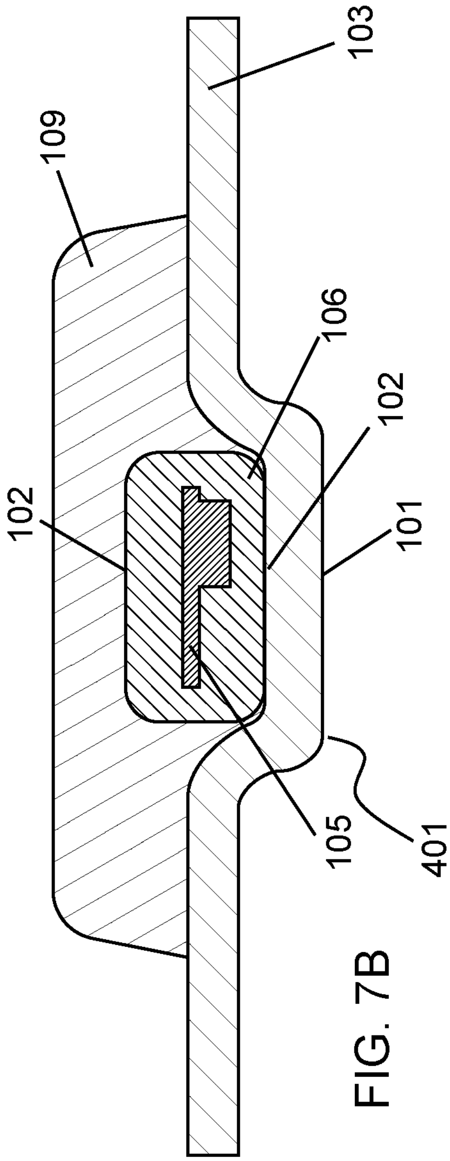
FIG. 7B is a cross sectional view of the apparatus of FIG. 5 along the line B-B.
Figure 8:
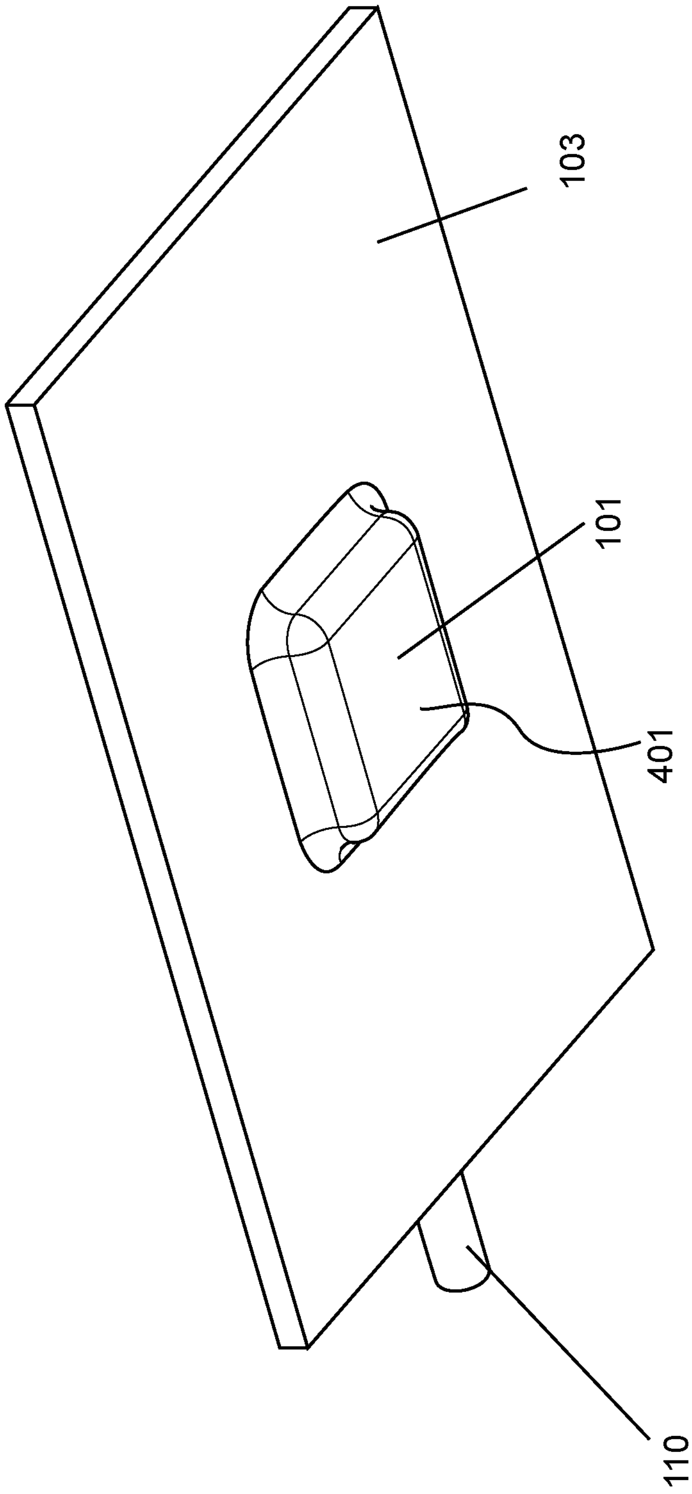
FIG. 8 is a bottom perspective view of the apparatus of FIG. 5.
Figure 17A:
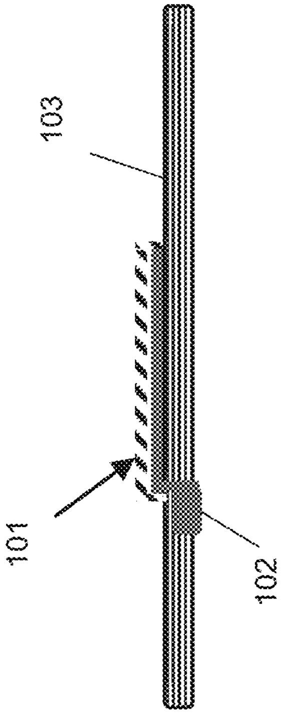
FIGS. 17A, 17B, 17C, and 17D are each side cross-sectional views of example electrodes according to the present disclosure.
Figure 17B:
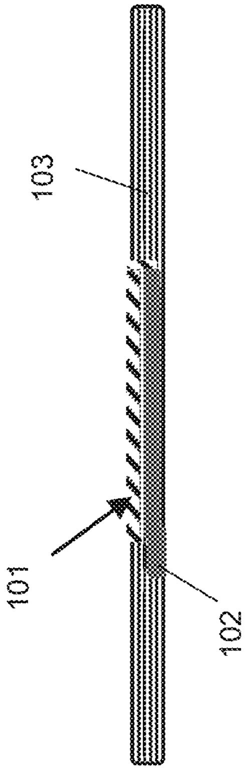
Figure 17C:
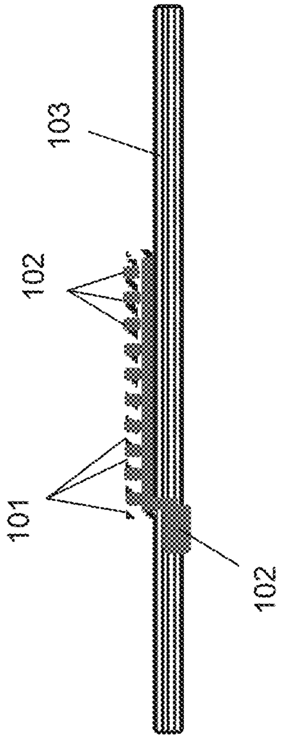
Figure 17D:
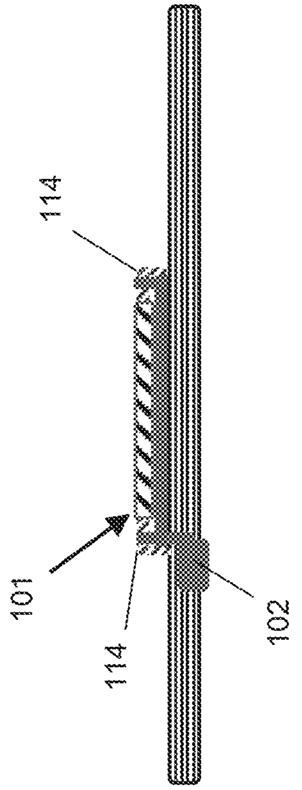

The arrangement of contact layer 101, conductive layer 102, and base layer 103 is not limited to the embodiment illustrated in FIGS. 3, 7A, and 7B. FIG. 17A illustrates an example electrode having a raised form factor, the electrode having a contact layer 101 of fabric knit or woven with TPE yarns; a conductive layer 102 comprising a layer of fabric behind it knit or woven with other conductive yarns, e.g., silver yarns; and a base layer 103 comprising non-conductive yarns. Conductive layer 102 may be connected to a patch of conductive fabric on base layer 103 for connecting the contact layer 101 to electronics. FIG. 17B illustrates another example textile electrode having a flat form factor with the same arrangement of contact layer 101, conductive layer 102 and base layer 103 as in FIG. 17B. FIG. 17C illustrates another example of textile electrode wherein contact layer 101 comprises both conductive TPE yarns and other conductive yarns, which as illustrated may be the same conductive yarn(s) as conductive layer 102 but may also be another type of conductive yarn. The structure of FIG. 17C creates a mixture of TPE and conductive non-TPE yarns in contact with skin of a user. FIG. 17D illustrates another example textile electrode wherein contact layer 101 comprises nonconductive TPE yarns 114 and non-TPE conductive yarn 102 that acts as the electrode.

Conductive layer 102 may be in electrical communication with active electrode board 105 via connection 104. Connection 104 may extend from conductive layer 102 through base layer 103 to active electrode board 105 to provide raw signal input from the contact layer 101/conductive layer 102 to active electrode board 105. Connection 104 may be a wire, an extension of conductive layer 102 directly soldered or crimped to active electrode board 105, a rivet, or other connection member coupling conductive layer 102 to active electrode board 105. Active electrode board 105 may comprise a printed circuit board (PCB) and electronic circuitry. Active electrode board 105 may also comprise a pre-amplifier, or communicate with a pre-amplifier, to record signal(s) with no attenuation from contact layer 101. Pre-amplification may improve signal-to-noise ratio from contact layer 101 as contact layer 101 is a dry electrode having increased impedance at the skin-electrode interface. Integration of active electrode board 105 places pre-amplifier in immediate proximity to the skin-electrode interface at contact layer 101 which may provide improved signal-to-noise ratio. Pre-amplified signal output 111, power input (e.g. Voltage Common Collector) 112, and ground wire 113 may each connect active electrode board 105 with co-axial cable 110 for communication with at least one of a computer, power source, and ground. In an embodiment, at least one of cable 110 and ground wire 113, may be made out of similar material as conductive layer 102, e.g. silver-plated nylon, polyester, Kevlar yarn and/or silver-plated copper microwire wrapped around polyester or nylon yarn.

In an embodiment, active electrode board 105 may be overmoulded with a non-conductive material to form overmould 106 as illustrated in FIGS. 3, 6, 7A, and 7B. Overmould 106 may be a non-conductive TPE. In an embodiment, overmould 106 is created using Technomelt™. Technomelt™ is a polyimide material with a low melting temperature e.g. about 110° C. Technomelt™ can be used in low pressure molding processes, making it compatible for use with active electrode board 105 as the temperature and pressure are low enough to not damage the components on the active electrode board 105 or affect the quality of their soldered joints. Overmould 106 may cover active electrode board 105 with about 1.0 to 1.5 mm coating of material. Wires connecting to the active electrode board 105 may protrude through overmoulding 106. Overmoulding 106 may waterproof the active electrode board 105 and provide strain relief for solder wire connections to a PC board of the active electrode board 105.

An electromagnetic shield 107 may be provided, the shield 107 defining overmould 106 and/or active electrode board 105 within an internal volume of the shield 107. In an embodiment, shield 107 may be made of sheet of silver or other conductive material such as conductive textile sheet (s). Shield 107 may be connected to active electrode board 105 by connection 108. Shield 107 may reduce electromagnetic interference between active electrode board 105 and contact layer 101.

In an embodiment, shield 107 may be formed as a portion of the PCB of active electrode board 105. In this embodiment, the PCB of active electrode board 105 may be a flexible PCB (e.g., made from a flexible and resilient material). In an embodiment, wings are configured to provide an electromagnetic barrier to reduce noise at the contact layer 101 to skin interface. The ground plane of active electrode board 105 may extend along the wings, and may form shield 107 by extending through overmould 106 to wrap around overmould 106.

Overmould 109 may be a non-conductive material. Overmould 109 may be formed from an overmoulded on base layer 103, shield 107, and co-axial cable 110 as shown on FIGS. 3, 5, 7A, and 7B. Overmould 109 may be a non-conductive TPE. Overmould 109 may provide an attachment to base layer 103, e.g. a textile, to secure overmould 106 and active electrode board 105 therein adjacent to base layer 103. In some embodiments, overmould 106 may not be fixed to base layer 103 and permitted to float with respect to base layer 103. In an embodiment, overmould 109 is a TPE having resilient and flexible properties, and overmould 109 may be configured to stretch when (textile) base layer 103 moves.

To join the overmould 106, active electrode board 105, and connection 104 to base layer 103, the overmould 106, active electrode board 105, and connection 104 are positioned in a mold and are then overmoulded (e.g., using injection molding technique) with a flexible elastomer material to form overmould 109. The elastomer material may adhere to a knit structure of base layer 103 creating an inseparable assembly which is waterproof. The elastomer material may be a thermoplastic elastomer (TPE) or a two part silicone epoxy.

The processing temperature of the TPE may be low enough to not damage base layer 103, e.g. a knit textile. For example, the TPE may be applied at a temperature lower than the melting temperature of the base layer 103. Adhesion between overmould 109 and base layer 103 may be mostly mechanical in nature. To encourage adhesion of the overmould 109 to base layer 103 a few methods may be used. For example, 1) base layer 103, e.g. a knit textile, could be pre-stretched to open up the knit structure allowing the TPE to flow into the yarns creating a mechanical interlock; 2) base layer 103 may be knit to have an open structure which allows the elastomer to flow into the yarns creating a mechanical interlock; 3) materials (i.e. yarns, coating) can be used in the base layer 103, which may have a knit structure that have a melting point similar to overmould 109, which allows some of the material of base layer 103 and the material of overmould 109 to melt together and then solidify as a mix.

Figure 24:
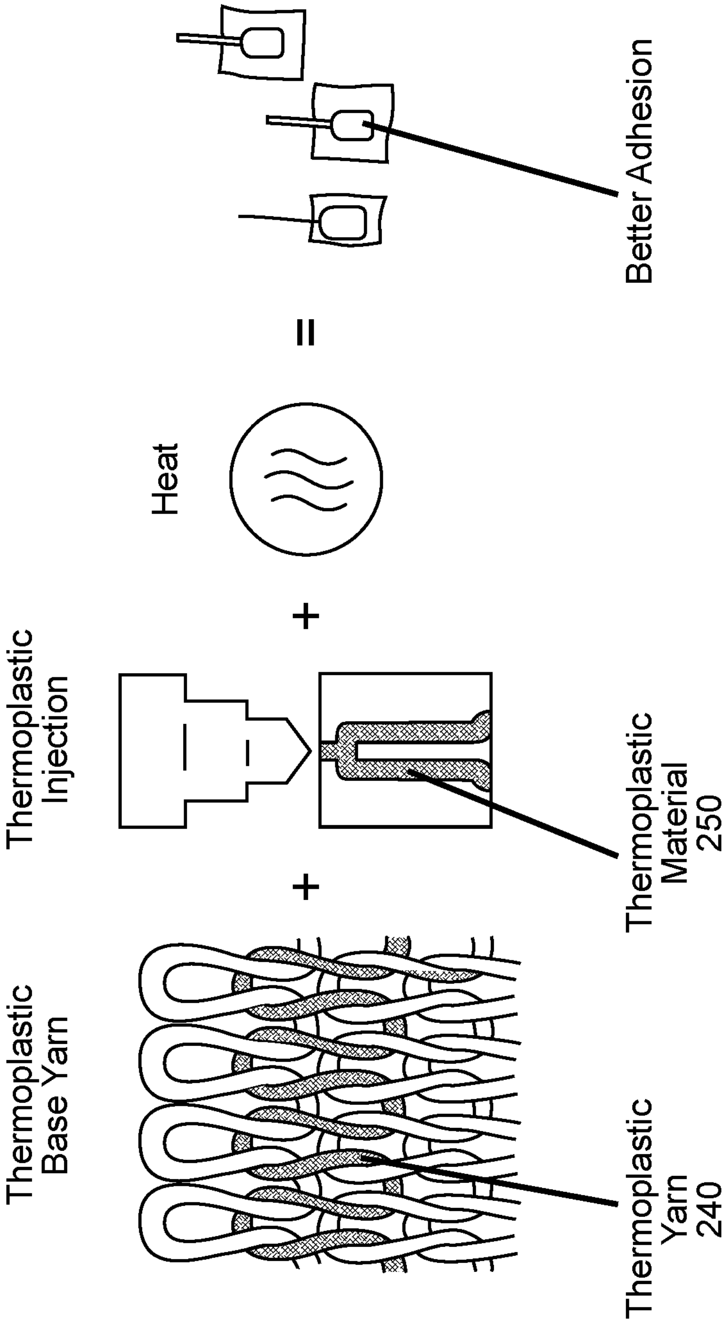
FIG. 24 shows an example thermoplastic yarn used in injection moulding.

In some embodiments, as shown in FIG. 24, in order to increase the adhesion between injected overmould 109 and the textile in base layer 103, a thermoplastic yarn 240 can be knitted in specific regions of base layer 103 to create chemical bonding in addition to mechanical bonding, such that overmould 109 and the thermoplastic yarn 240 in base layer 103 may share chemical composition. In this example embodiment, when brought to a mutual melting temperature during injection molding, the thermoplastic material 250 in overmould 109 and the thermoplastic yarn 240 in base layer 103 can mix at the chemical and mechanical level.

Contact layer 101 may comprise TPE(s). A variety of thermoplastic elastomer materials may be used in contact layer 101. Conductive filler may also be blended with the TPE material of contact layer 101 to impart desired conductivity properties. TPE polymer may be provided in pellets/granules which may be melted into molten form and mixed with conductive carbon based fillers to form a homogenous mixture. The homogeneous mixture comprising blended TPE(s) and conductive filler may be formed into a filament yarn. In an embodiment, an extruded filament yarn is formed from the blended TPE and conductive filler. Extruded filament may be knitted as contact layer 101 of electrode 100 having a desired knit pattern suitable for biosensing. U.S. Patent Publication No. US2011/0200821 describes an example system and process that may be used for manufacturing conductive filament yarn, the entire disclosure of which is hereby incorporated by reference herein.

TPE materials for contact layer 101 may be neat polymer matrix materials belonging to two groups; (1) Styrenic Block copolymers, and (2) Polyolefin-Based Elastomers. TPE material may also be thermoplastic polyurethane Elastomers (TPU), thermoplastic polyether ester/polyimide elastomer, and silicon base materials such as Polydimethylsiloxane (PDMS).

Conductive filler may be an electrically conductive material and may form 0.5 wt % to 40 wt % of contact layer 101. In an embodiment, conductive filler may be carbon black particles. Carbon-based materials such as carbon nanotubes, graphene, carbon black, acetylene black, and mixture thereof may also be as conductive filler. Conductive filler is not limited to carbon material, and may be metallic nanofillers such as silver, gold or brass. Conductive fillers may be selected based on (1) biocompatibility of the conductive filler, (2) size and morphology, (3) surface area, (4) percolation rate, (5) conductivity, (6) spinnability.

In an embodiment, contact layer 101 may comprise a filament (or filament yarn) comprising TPE(s) and conductive filler that may have at least one of a Monofilament Diameter of less than or equal to 0.5 mm, more preferably 0.1-0.4 mm; elastic limit (recoverable stretch) of 100% min, preferably greater than 150%; filament conductivity of 1-100 KOhm/m; and rheology—as measured, e.g., by viscosity and melt flow index, suitable for forming filament yarn when melted.

Figure 10:
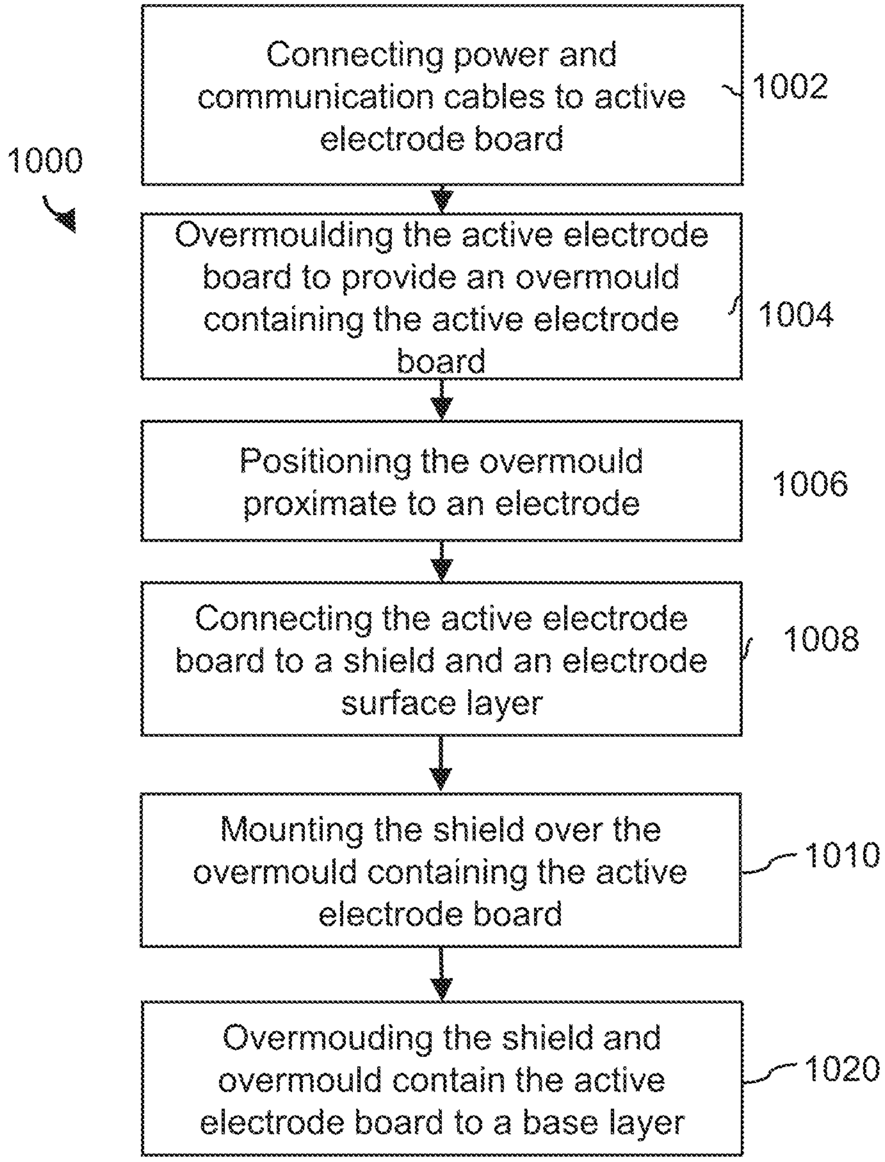
FIG. 10 is a flow chart depicting a method of manufacturing an apparatus according to the present disclosure.

FIG. 10 is a flow chart depicting an example process 1100 for manufacturing an apparatus according to the present disclosure.

Figure 9:
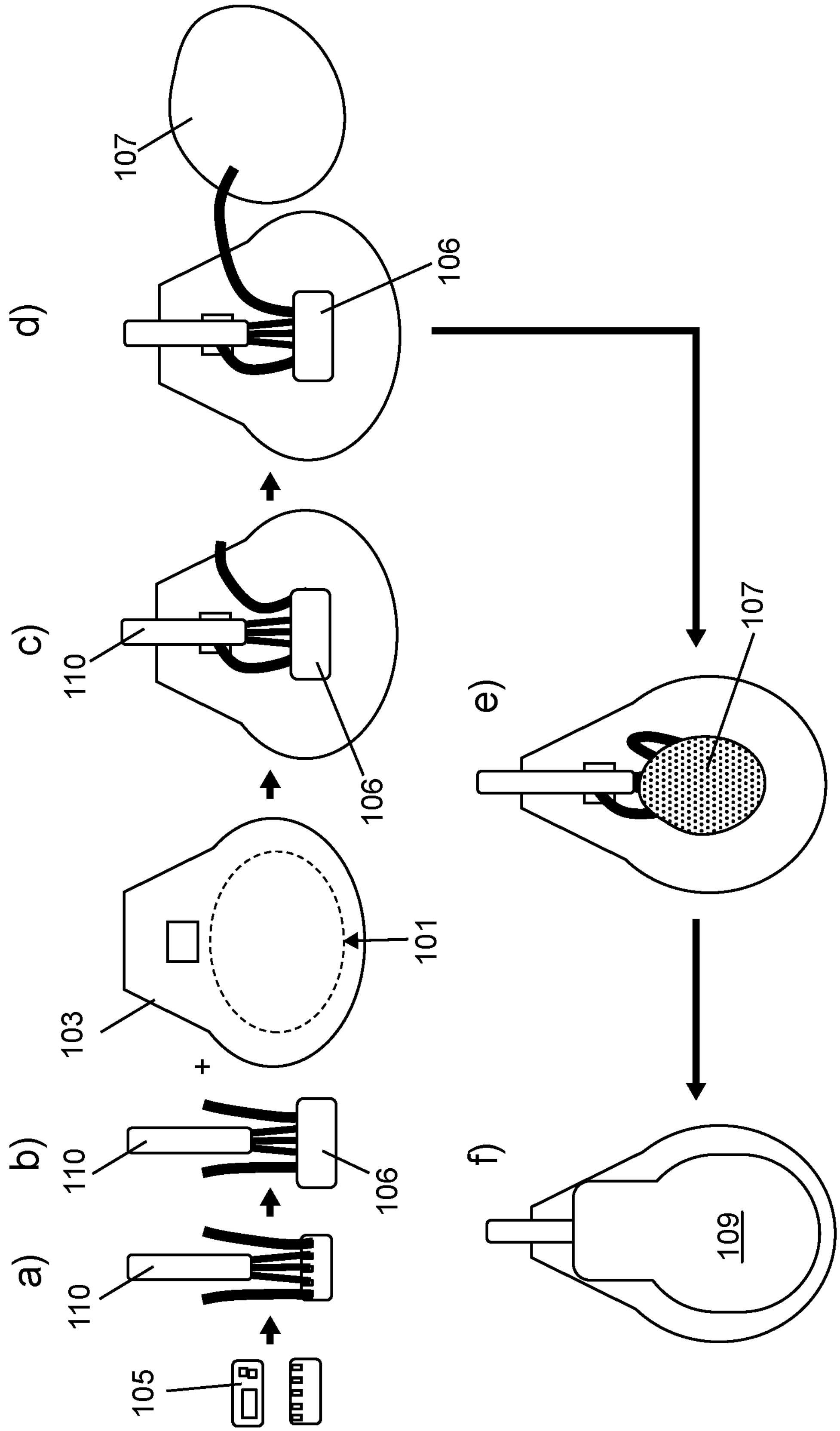
FIG. 9 is an illustration of an example sequence of making an apparatus according to the present disclosure.

At block 1002, power and communication cables 110 are connected to an active electrode board 105 as illustrated at FIG. 9 *a*)

At block 1004, the active electrode board 105 is overmoulded to provide an overmould 106 containing the active electrode board as illustrated at FIG. 9 *b*).

At block 1006, the overmould 106 is positioned proximate to a contact layer 101. For example overmould 106 may be positioned on an opposing side of an electrode's contact layer 101 as illustrated in FIG. 9 *c*).

At block 1008, the active electrode board 105 is connected to an electromagnetic shield 107 and electrode contact layer 101 as illustrated in FIG. 9 *d*).

At block 1010, the electromagnetic shield 107 is mounted over the overmould 109 as illustrated in FIG. 9 *e*).

At block 1020, the shield 107 and overmould 109 containing the active electrode board 105 are overmoulded to a base layer 103 as illustrated in FIG. 9 *f*).

Figure 11:
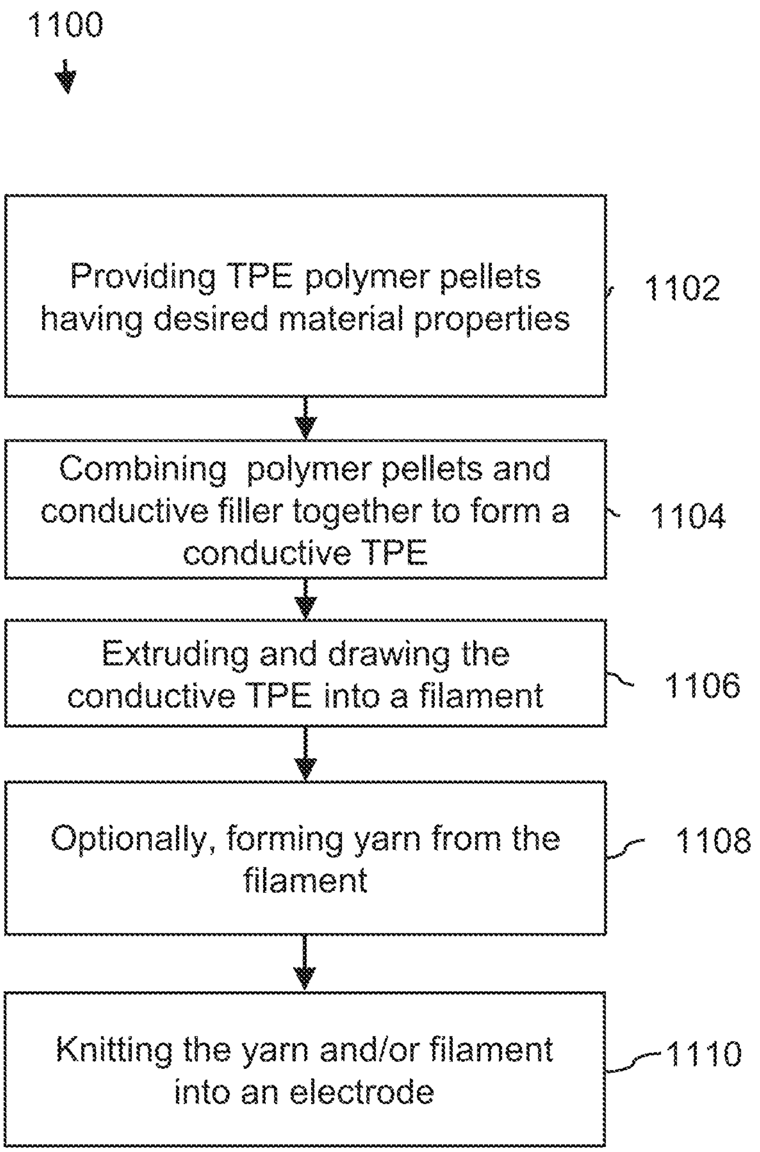
FIG. 11 is a flow chart depicting a method of manufacturing an electrode.

FIG. 11 is a flow chart depicting an example process 1100 for manufacturing an electrode. At block 1102, TPE polymer pellets having desired thermoplastic elastomer material properties are provided.

Figure 12:
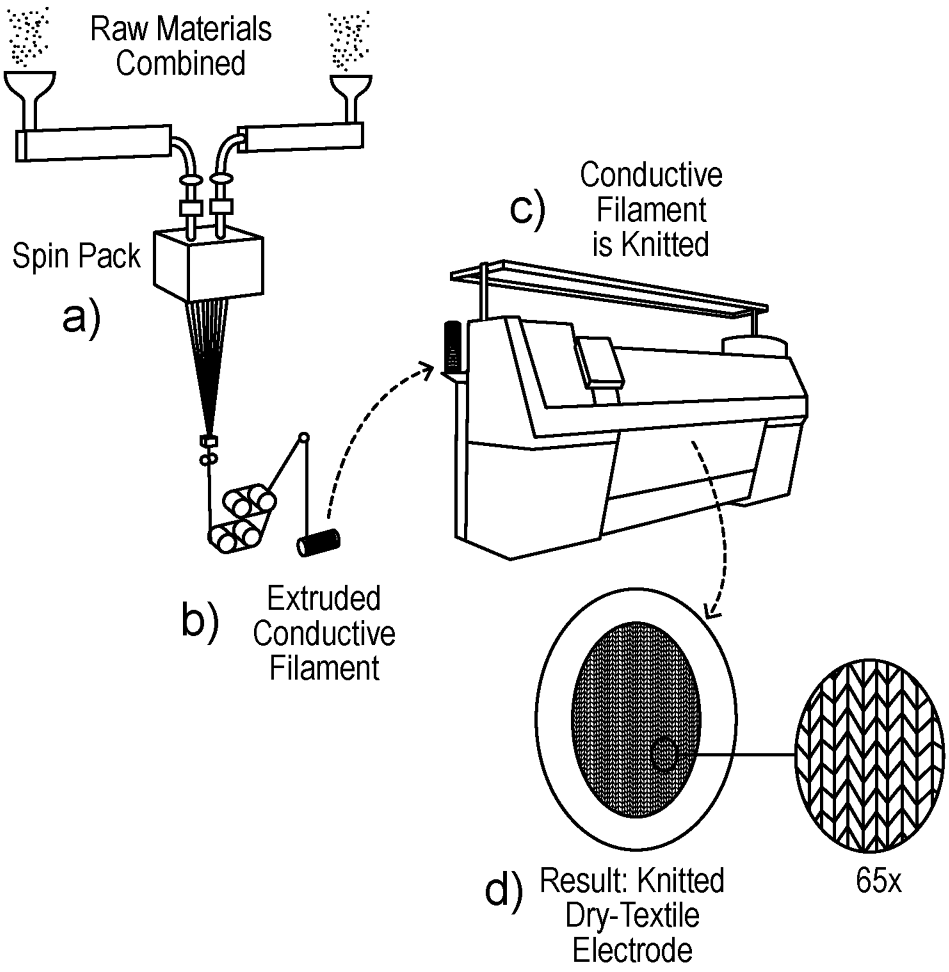
FIG. 12 is an illustration of an example sequence of making an electrode.
Figure 13:
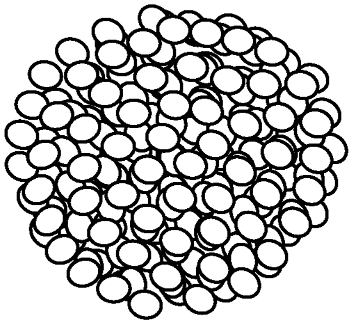
FIG. 13 is a view of conductive polymer formed from thermoplastic elastomeric polymer pellets compounded with conductive filler.

At block 1104, polymer pellets and conductive filler are combined together to form a conductive TPE. In an example, the TPE polymer pellets and conductive filler may be compounded to mix the conductive fillers with TPE polymer forming conductive polymer pellets shown in FIG. 13. The conductive polymer pellets may be added to a hopper for of a melt spinning machine as shown in FIG. 12 *a*). In an embodiment, the melt spinning machine can be mono-, bi-, tri-, quad-components. Depending on the desired properties of the filament and/or filament yarn, the composition of the yarn may be selected from different components. Each component may have a separate hopper/feeder and heating zone to melt each of the components together—including the conductive polymer pellets which is melted to form conductive TPE. In an embodiment, the TPE polymer pellets and conductive filler may be melted at a temperature from 130 C to 300 C. In another embodiment, the TPE polymer pellet and conductive filler may be melted together at a temperature below 130 C. Components of the filament yarn may include conductive polymer (such as conductive TPE), self-healing materials, far infrared (FIR) particles and microcapsules of phase-change materials for thermal regulation.

Figure 15B:
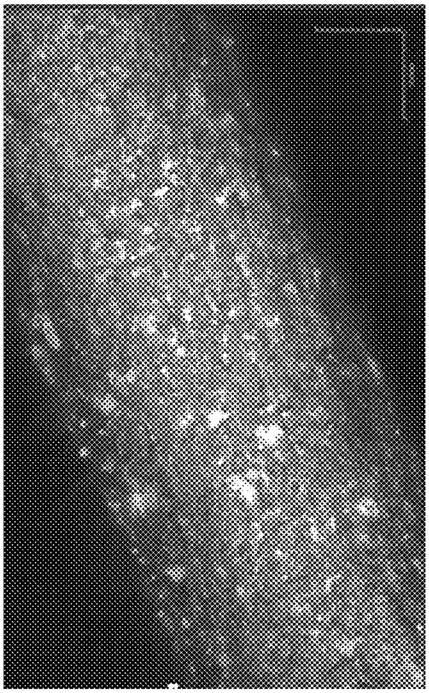
FIGS. 15A and 15B are each enlarged images of an example filament comprising thermoplastic elastomeric and conductive filler.
Figure 15A:
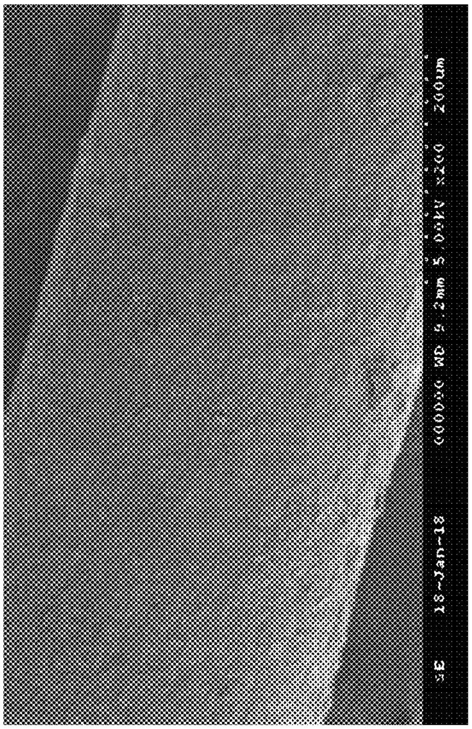

At block 1106, the conductive TPE may be extruded and drawn into a filament. Continuing the above example, as illustrated in FIG. 12 *a*), the conductive TPE may be extruded and drawn in the melt spinning machine to form filament(s), which may be combined with filaments of other components at a spinneret (shown in FIG. 12 *a*) to form a filament yarn as discussed at block 1108, which may then be directly solidified by cooling. Different filament structures may be created, such as monocomponent with different diameters (e.g. 50 microns to 400 microns) and bicomponent structures (e.g. core-sheath, lobal, side-by-side, segmented, and Islands-in-the-sea). FIGS. 15A and 15B illustrate microscopic images of extruded mono-filament (single component) comprising conductive TPE.

In an example, the spinneret can be configured to provide a different cross sectional shapes and diameters of extruded filaments. In an embodiment, diameter of the spinneret can be between 50 micron to 1 mm. The extruded filament may be drawn to improve the crystallinity and create thinner filaments. In an embodiment, the diameter of the extruded filament may be drawn to have a diameter in the range of 100 to 500 micron. In an example, the properties (e.g. spinnability, biocompatibility, and conductivity) of a monocomponent filament structure may solely depend on the type of TPE matrix and fillers used.

Filaments according to the present disclosure may have different bicomponent structures. Sometimes conductive pellets may not have sufficient mechanical strength to be extruded and drawn only by themselves; accordingly, another polymer may be used as a core material and the conductive polymer of the conductive pellets (which is made through compounding) may be a sheath. Filaments may have various structures such as hollow-fibers or a structures formed from polymer filaments extruded together in multi-component melt-spinning. The filaments may have various cross-section such as, for example, side-by-side, core and sheath, hollow, c-shape, trilobal, islands in the sea, and the like. In an example, an extruded filament may comprise water soluble polymer(s) (e.g. Poly(vinyl alcohol); "PVA") which may be placed in a water bath after extrusion to remove the water soluble polymer(s). In another example, air may be blown during spinning to create hollow fibers where the sheath is formed from conductive polymer.

Figure 14:
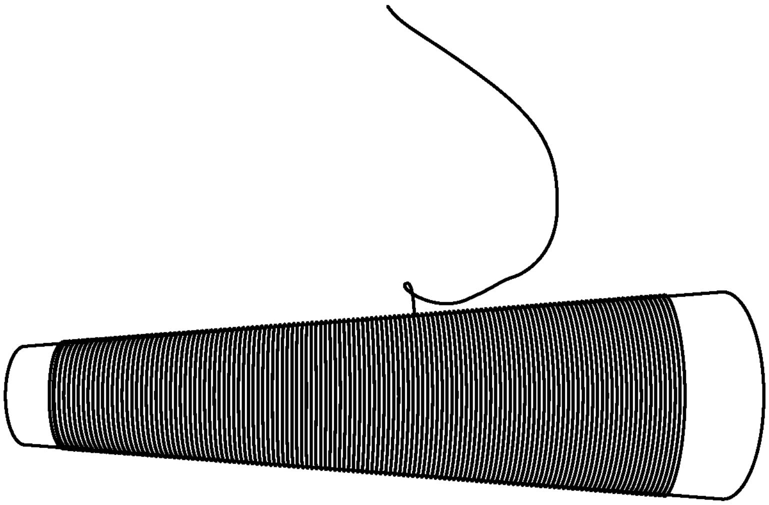
FIG. 14 is a perspective view of an example filament comprising thermoplastic elastomeric and conductive filler.

At block 1108, optionally filament yarn is formed from the filament(s). Yarn may be formed by a melt spinning machine illustrated at FIG. 12 *a*). In an embodiment, after extruding the filament, the filament may be wrapped by water soluble polymer(s), e.g. PVA to make a yarn. In an example, mono-component filament comprising conductive TPE may be a core wrapped by water soluble yarns (e.g. PVA) to make the yarn formed from the filament easier to knit. In an embodiment, extruded filament may be coated with powder for better knittability. In an embodiment, the powder is Talc powder. As shown in FIG. 12 *b*), the filament(s) or filament yarn may be further extruded to a desired dimension. FIG. 14 illustrates an example filament yarn comprising conductive TPE produced according to the disclosure herein.

Figure 16B:
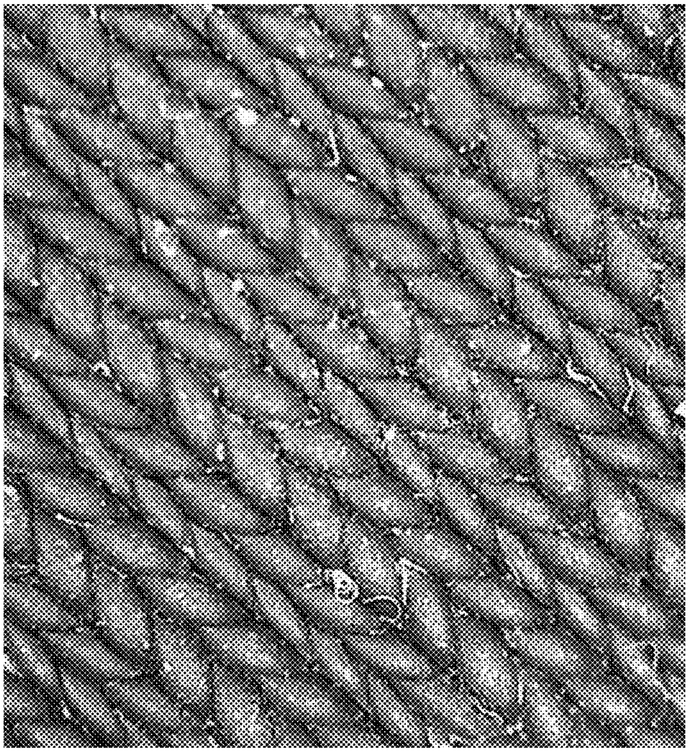
FIGS. 16A and 16B are each enlarged images of an example patterns of knit filament.
Figure 16A:
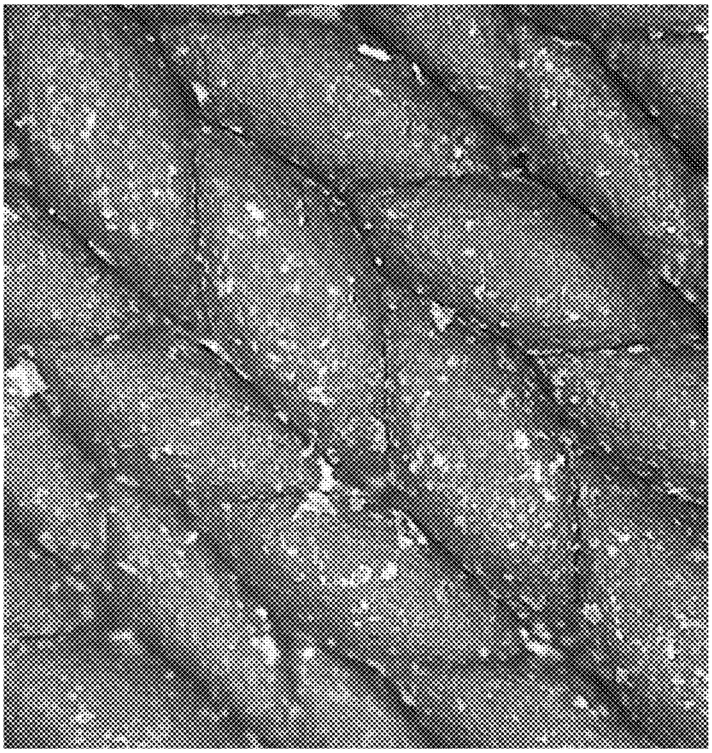

At block 1110, the yarn and/or filament is knit into an electrode. In an example, flat-bed knitting machines illustrated in FIG. 12 *c*) may knit yarn or filament comprising conductive TPE into electrodes (shown in FIG. 12 *d*)) having a desired geometry and pattern. Based on the diameter of yarn the gauge of the knitting machine can be chosen. The thinner the yarn or filament, the higher the gauge of the machine to increase the resolution of the knitted electrode. In an example, different structures of electrode may be knit such as an electrode having a raised form factor or a flat form factor. The electrode may be made with various other textile manufacturing processes such as jacquard weaving, circular jacquard knitting, warp knitting and embroidery based on the desired properties of the electrode. For example jacquard weaving may be used to provide structures having improved dimensional stability; circular knitting may provide a structure with improved flexibility that may be produced quickly; and warp knitting may provide different yarn diagonals into knitted structures. Flat bed knitting may be used to apply different functionalities into the electrode, such as by inserting a functional laminate, RFID, and/or pH/sweat/moisture sensor behind the electrode during the manufacturing process. The size of the electrode, its geometry (e.g. square, oval, circular) may also be selected to improve performance for example by minimizing impedance at the skin-electrode interface. Yarn and/or filament may be knit into a desired pattern. Example patterns of knit filament are shown in FIGS. 16A and 16B which are enlarged views of a knit pattern under 225× and 15-65× magnification respectively. The size, shape and materials of the yarn may be selected to enhance the performance of the electrode for receiving and/or recording a specific type of signal based on its frequency and amplitude range. In an example, an electrode comprises conductive thermoplastic elastomer, and the amount of conductive fillers, type of conductive filler, and structure of the yarn or filament such as diameter, elongation, tensile strength, cross-section, and geometrical structure may be varied to suit a desired application e.g. ECG, EMG, EEG, FES, and so on.

In some embodiments, instead of using overmould 109 to cover the active electrode board 105 when disposed on base layer 103, a laminate material may be used.

Figure 18A:
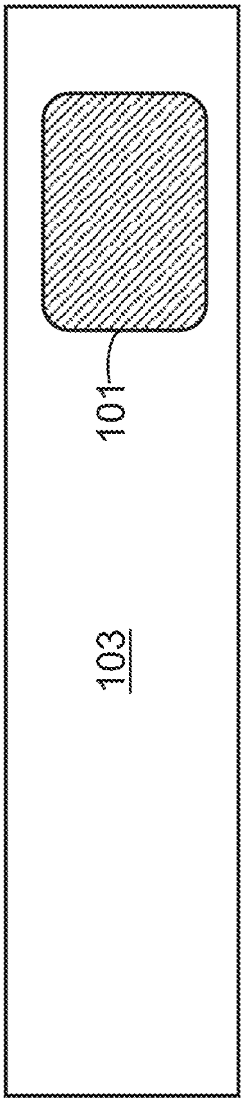
FIG. 18A shows a bottom view of an example contact layer (electrode) attached to a base layer according to the present disclosure.

Referring now to FIG. 18A, which shows a bottom view of base layer 103, according to some embodiments. This view show a surface of base layer 103 for contacting skin during use. As shown, an example contact layer 101 attached to a base layer 103. Contact layer 101 may be an electrode configured to convert ionic current at a skin-electrode interface to electrical signals when the electrode is coupled to a user. In some embodiments, contact layer 101 may be made of yarn having a conductive filler. For example, contact layer 101 may be made of conductive TPE yarn comprising a TPE combined with conductive filler. In another embodiment, contact layer 101 may comprise conductive material coated onto a TPE.

In an embodiment, base layer 103 may be a non-conductive double layer fabric. Double layer fabric can provide protected space in-between the two layers where certain materials can be inlaid or knitted without being exposed or visible on the surface of the fabric. For instance, having a double layer allows knitting trace or bus yarns to act as wires embedded within the garment in-between the two layers. A single layer knitting would expose these traces either outside or inside of the garment. Base layer 103 may be part of an article, e.g. clothing or furniture, having a surface area.

Figure 18B:
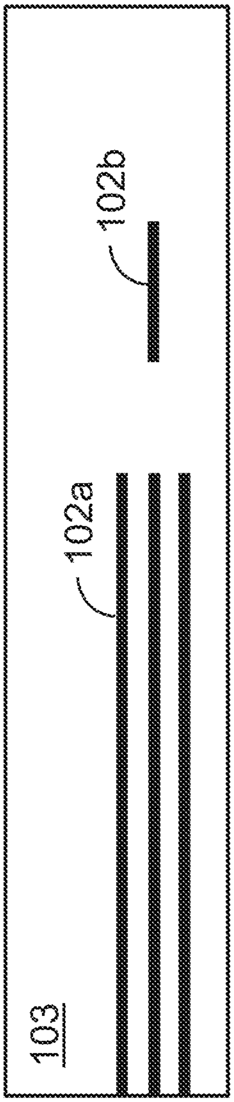
FIG. 18B is a cross-sectional view of the base layer in FIG. 18A showing conductive layers (traces) according to the present disclosure.

FIG. 18B shows a horizontal cross-sectional view (parallel to the view of FIG. 18A) of the base layer 103 in FIG. 18A having conductive layers (traces) 102*a*, 102*b*. In an embodiment, conductive layers 102*a*, 102*b* may be made of silver, such as silver-plated nylon, polyester, Kevlar yarn and/or silver-plated copper microwire wrapped around polyester or nylon yarn. Conductive layer 102*a*, 102*b* may be defined beneath contact layer 101. Contact layer 101 and conductive layers 102*a*, 102*b* may be mounted on base layer 103 as shown in FIG. 18D. In an embodiment, conductive layers 102*a*, 102*b* may be substantially similar to conductive layer 102 as shown in FIG. 3. Conductive layers 102*a*, 102*b* may be connected to a patch of conductive fabric on base layer 103 for connecting contact layer 101 to electronics within an active electrode board 105.

Figure 18C:
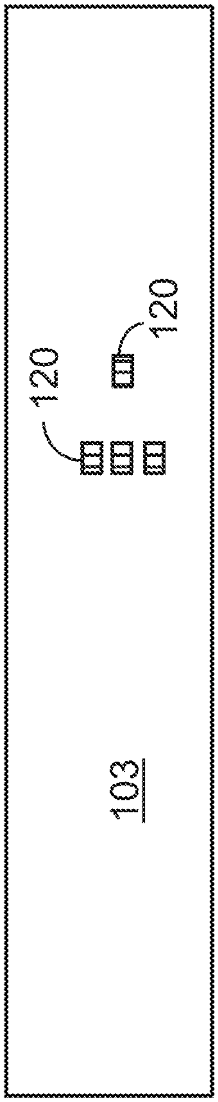
FIG. 18C is a view of base contact pads attached to the base layer in FIG. 18A.
Figure 18D:
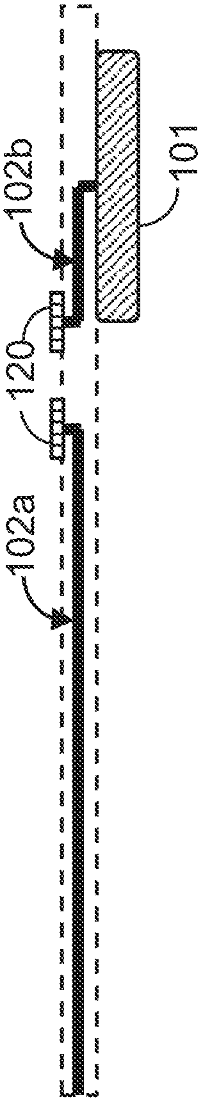
FIG. 18D is a cross-sectional view of the base layer in FIG. 18A showing the conductive layers, the base contact pads, and the contact layer.

FIG. 18C is a view of base contact pads 120 attached to the base layer 103 in FIG. 18A. The base layer 103 may have one or more base contact pads 120. Each of the base contact pads 120 may be connected to be in electrically communication to a respective conductive layer 120*a*, 120*b* as shown in FIG. 18D. Each base contact pad 120 may be made of knitted yarns that have a conductive filler. For example, base contact pads 120 may include copper microwire.

FIG. 18D is a vertical cross-sectional view 140 (orthogonal to the view of FIG. 18A) of the base layer in FIG. 18A showing the conductive layers 102*a*, 102*b*, the base contact pads 120, and the contact layer 101. As shown in FIG. 18D, contact layer 101 is in electrical communication with a conductive layer 102*b*. As shown in FIG. 18D, contact layer 101 may have a raised form factor such that contact layer 101 defines a surface in a plane above (Le, more proximate to a user than) base layer 103. A raised form factor may promote sustained contact between contact layer 101 and a user.

Figure 19A:
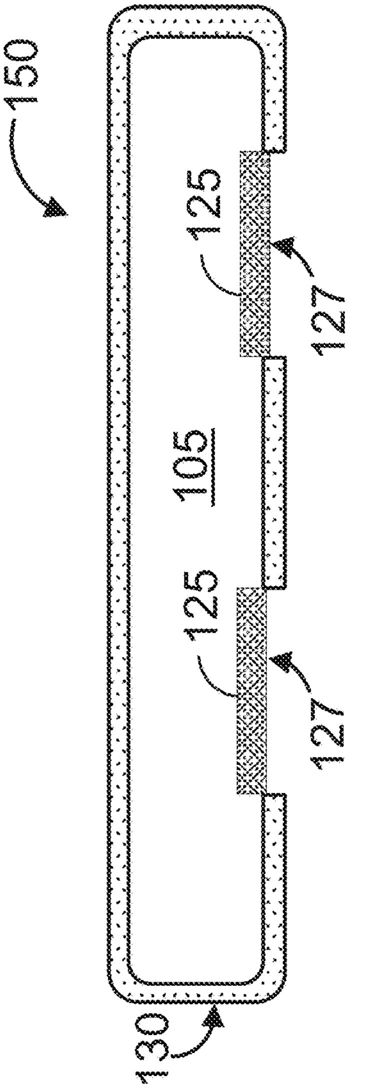
FIG. 19A is a cross-sectional view of an example coated active electrode board showing two of the board contact pads.

FIG. 19A is a vertical cross-sectional view of an example coated active electrode board 150 having two board contact pads 125, according to some embodiments. The active electrode board 105 may be coated with a conformal coating 130, which may include material that is silicone-based, fluorinated-polymer-based, or acrylated-urethane-based. The conformal coating 130 may act to protect the active electrode board 105 and its electrical and electronic components from water and dust. This conformal coating 130 may exclude or expose a part of the board contact pads 125 used for connection to the base contact pads 120 on the base layer 103. For example, each board contact pad 125 may have a contact surface (board contact surface) 127 used for connection to the base contact pads 120 on the base layer 103, and the contact surface 127 is not covered by the conformal coating 130.

Figure 19B:
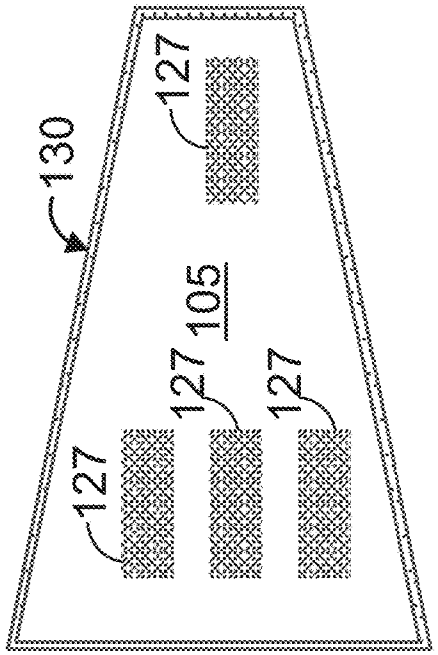
FIG. 19B is a bottom view of the example coated active electrode board in FIG. 19A.

FIG. 19B is a bottom view of the example coated active electrode board 150 in FIG. 19A showing a plurality of board contact surfaces 127. As discussed in detail below, each board contact surface 127 may be bounded or otherwise connected to a corresponding surface area of the base contact pads 120 using a solder paste.

Figures 20A, 20B:
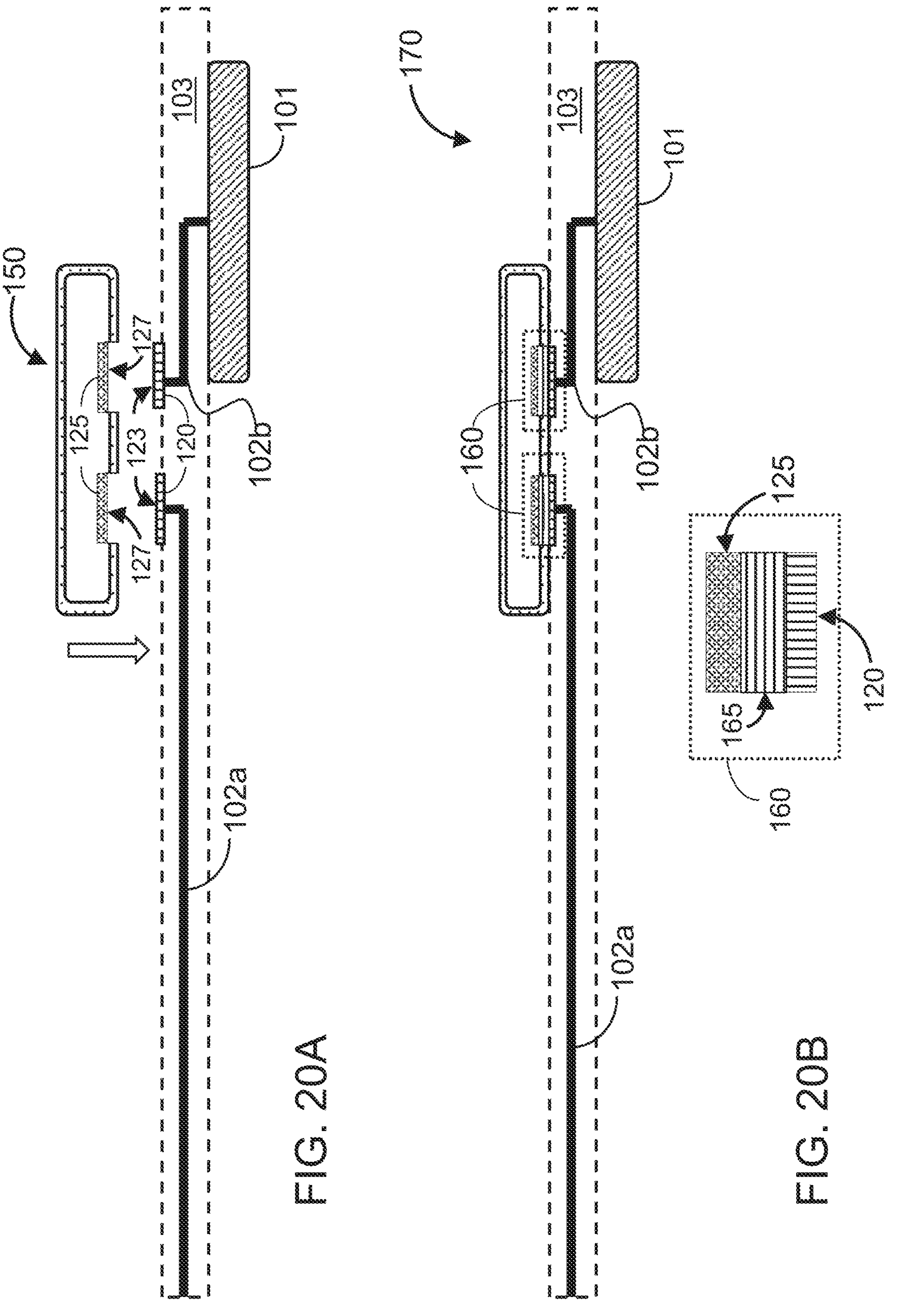
FIG. 20A is a cross-sectional view of an example coated active electrode board positioned on top of a base layer.
FIG. 20B is a cross-sectional view of the example coated active electrode board in FIG. 20A in position for attachment to the base layer.

FIG. 20A is a vertical cross-sectional view of an example coated active electrode board 150 positioned on top of a base layer 103. As shown, the base contact pad 120 may include a base contact surface 123 configured to provide mechanical and electrical communication with a board contact surface 127 of the board contact pad 125. In some embodiments, the base contact surface 123 and the board contact surface 127 are configured to correspond or match in terms of size, surface area and/or dimensions. For example, the base contact surface 123 and the board contact surface 127 may be configured to have corresponding surface size and/or surface shape. For example, the base contact surface 123 and the board contact surface 127 may be configured to have identical surface size and/or surface shape.

As the coated active electrode board 150 is positioned for connecting to the base layer 103, the base contact surface 123 and the board contact surface 127 are aligned so that they may be connected, coupled or bounded using a solder paste, as shown in FIG. 20B.

FIG. 203 is a cross-sectional view of the example coated active electrode board 150 in FIG. 20A in position for attachment to the base layer 103. The base contact surface 123 and the board contact surface 127 are bounded in a coupling mechanism 160, the coupling mechanism 160 may be made using a solder paste 165 applied at a low temperature within a range of 130 to 170 degrees Celsius.

Low temperature solder paste 165 can help ensure that the base contact surface 123 and the board contact surface 127 are bounded without burning the textile in the base layer 103.

In some embodiments, commercially available solder paste may be used for the coupling mechanism 160. For example, the table below shows examples of commercially available solder paste that can be used as low temperature solder pastes.

| Manufacturer - Product Number | Composition | Melting Point |
|---|---|---|
| Chip Quick Inc.-NC191LTA35 | Bi57Sn42Ag1 - T4 Mesh Size | 137° C. |
| Chip Quick Inc. - NC191LTA15T5 | Bi57Sn42Ag1 - T5 Mesh Size | 137° C. |
| SRA Solder Products- SSLTNC-T5-15G | Sn42Bi57Ag1- T5 Mesh | 137° C. |
| Kester Solder- 70-0102-0311 | Sn62-Pb36Ag2-T3 Mesh | 179° C. |

Even though multiple base contact pads 120 and multiple board contact pads 125 are shown throughout the drawings, it is to be appreciated that only one base contact pad 120 and only one board contact pad 125 are necessary for transmission and sending signal connection from the contact layer 101 to the active electrode board 105.

Once attached at the base contact pads 120 and board contact pads 125, the overall structure 170 may be referred to as a connected structure 170.

Figure 21:
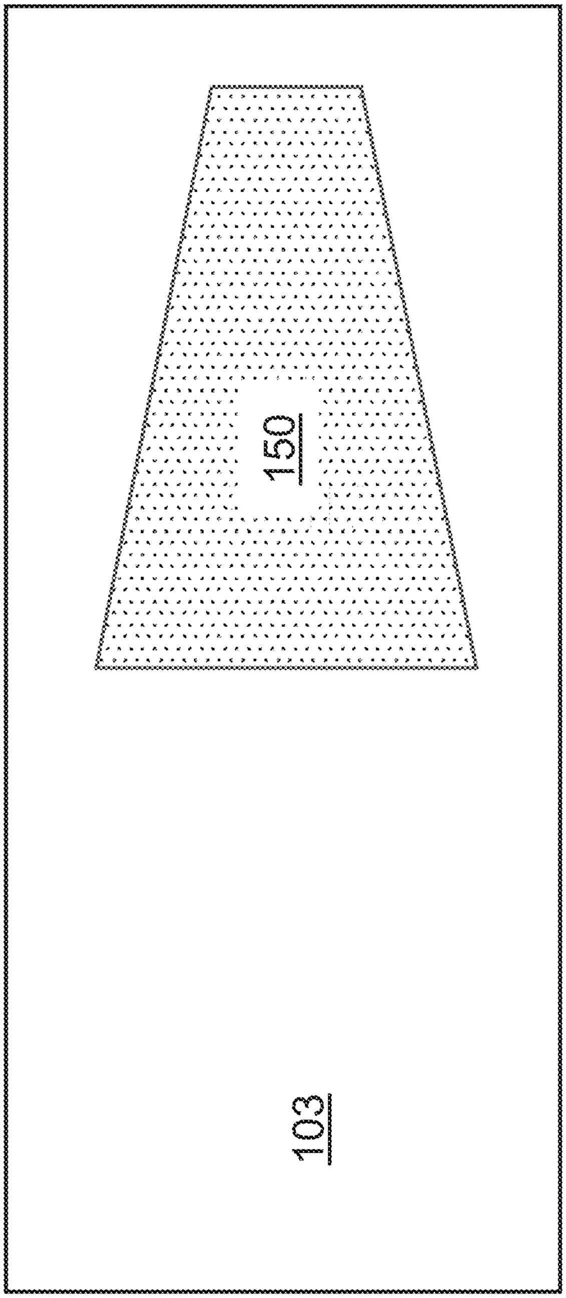
FIG. 21 is a top view of the example coated active electrode board in FIG. 20A in position for attachment to the base layer.

FIG. 21 is a top view of the example coated active electrode board 150 in FIG. 20A in position for attachment to the base layer 103 in a connected structure 170.

Figure 22A:
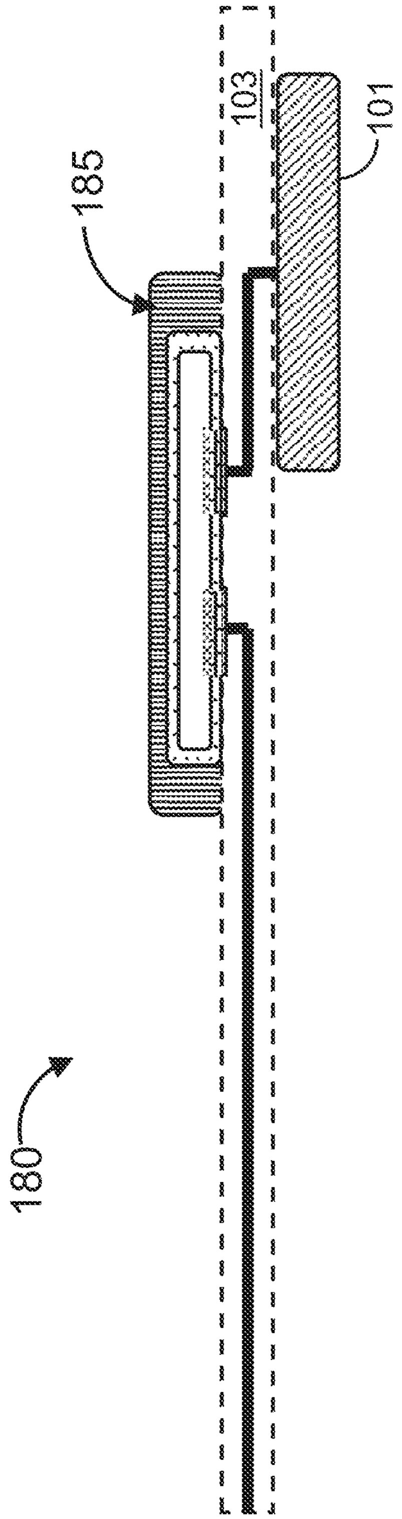
FIG. 22A is a cross-sectional view of the example coated active electrode board in FIG. 20A being attached to the base layer using a laminate material.

In some embodiments, the coated active electrode board 150 in the connected structure 170 is attached to the base layer 103 using a laminate material 185. FIG. 22A is a cross-sectional view 180 of the example coated active electrode board 150 being attached to the base layer 103 using a laminate material 185.

Figure 22B:
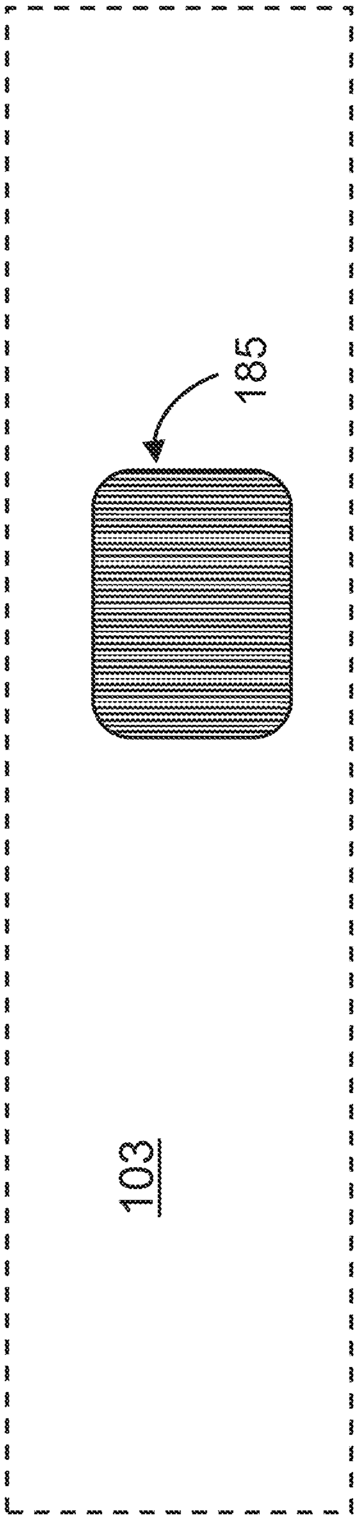
FIG. 22B is a top view of the example coated active electrode board in FIG. 22A being attached to the base layer using a laminate material.

FIG. 22B is a top view of the example coated active electrode board 150 being attached to the base layer 103 using a laminate material 185. As shown, the laminate material 185 conforms to connected structure 170, and covers all the surfaces of the coated active electrode board 150 except the surface bounded to the base layer 103. The laminate material 185 provides protection of the coated active electrode board 150 against strain, scratch, dust, and light.

Laminate material 185 may be a non-conductive material. In some embodiments, the laminate material 185 may be stretch films made out of one or more polymer material, such as Thermoplastic Polyurethane (TPU), other Polyurethane, Acrylic, Vinyl, polyethylene, polyvinyl chloride, or elastomers. In some embodiments, laminate material 185 may also be made out of another textile material. The laminate material 185, when used in small areas, are sufficiently thin and flexible as to not negatively affect fabric behavior of the textile in base layer 103.

In an embodiment, laminate material 185 is a TPU having resilient and flexible properties, and laminate material 185 may be configured to stretch when (textile) base layer 103 moves.

In some embodiments, the laminate material 185 and the base layer 103 can be bounded using heat activated glue. For example, laminate material 185 can be applied by first applying a glue to the surface area that will touch the base layer 103, then positioned in the desired area, facing down towards textile of the base layer 103, and then heat pressed to activate the glue.

In some embodiments, the glue may be chosen to be compatible with the material of the textile substrate in base layer 103. For example, the textile may be composed of: 69% nylon, 26% spandex, and 5% other.

As shown in FIG. 22A, the laminate material 185 covers a portion of the base layer 103 around the coated active electrode board 150. This covered portion of base layer 103 around the coated active electrode board 150 may have a margin ranging from 1 to 5 mm around the coated active electrode board 150.

Figure 23:
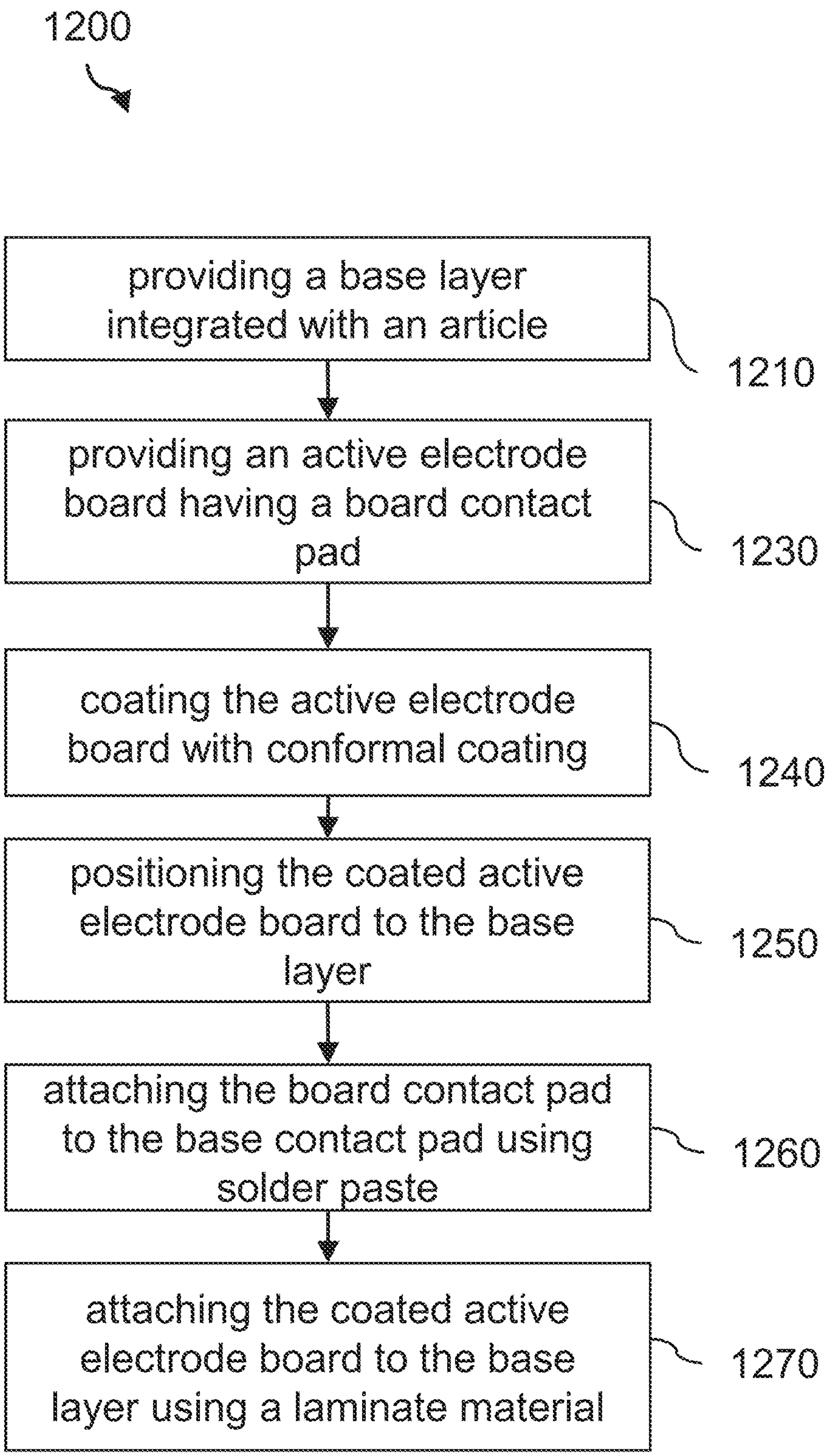
FIG. 23 is a flowchart showing an example process of manufacturing an example article having a coated active electrode board attached to a base layer.

FIG. 23 is a flowchart showing an example process 1200 of manufacturing an example article having a coated active electrode board 150 attached to a base layer 103.

At step 1210, a base layer 103 integrated with an article is provided. In some embodiments, the base layer 103 may be a non-conductive fabric. Base layer 103 may be part of an article, e.g. clothing or furniture, having a surface area. The base layer 103 may include textile.

The base layer 103 may be integrated with a contact layer 101 in the article. For example, the base layer 103 and the contact layer 101 may be knitted together by the same machine to form part of the article. For another example, the contact layer 101 may be mounted to the base layer 103.

The contact layer 101 may include conductive TPE yarn comprising a TPE combined with conductive filler. In another embodiment, contact layer 101 may comprise conductive material coated onto a TPE.

In some embodiments, the contact layer 101 is in electrical communication with conductive layers 102*a*, 102*b* mounted on the base layer 103. In some embodiments, the conductive layer 102*a*, 102*b* may include silver yarn.

In some embodiments, the conductive layers 102*a*, 102*b* may be silver-plated nylon, polyester, Kevlar yarn and/or silver-plated copper microwire wrapped around polyester or nylon yarn. Conductive layers 102*a*, 102*b* may be defined beneath contact layer 101. Contact layer 101 and conductive layers 102*a*, 102*b* may be mounted on base layer 103.

In some embodiments, contact layer 101, conductive layers 102*a*, 102*b* and base layer 103 may be knitted together within the article.

The contact layer 101 may have a raised form factor such that contact layer 101 defines a surface in a plane above (i.e. more proximate to a user than) base layer 103. A raised form factor may promote sustained contact between contact layer 101 and a user.

Conductive layers 102*a*, 102*b* may be connected to a patch of conductive fabric on base layer 103 for connecting the contact layer 101 to electronics.

At step 1230, an active electrode board 105 having a board contact pad 125 is provided. Active electrode board 105 may have a printed circuit board (PCB) and electronic circuitry. Active electrode board 105 may also include a pre-amplifier, or communicate with a pre-amplifier, to record signal(s) with no attenuation from contact layer 101.

At step 1240, the active electrode board 105 is coated with a coating material 130 which may be a conformal coating. The conformal coating material may be silicon-based, fluorinated polymer-based or acrylated urethane-based, where the coating exposes a surface 127 of the board contact pad 125. The coating 130 may act to protect the active electrode board 105 and its electrical and electronic components from water and dust. This coating 130 may exclude or expose a part of the board contact pads 125 used for connection to the base contact pads 120 on the base layer 130. For example, each board contact pad 125 may have a contact surface (board contact surface) 127 used for connection to the base contact pads 120 on the base layer 130, and the contact surface 127 is not covered by the coating 130.

At step 1250, the coated active electrode board 150 is positioned relative to the base layer 103, where the board contact pad 125 of the coated active electrode board 150 aligns with a base contact pad 120 of the base layer 103.

In some embodiments, the base contact pad 120 may include conductive knitted yarn.

In some embodiments, the conductive knitted yarn may include copper microwire.

In some embodiments, the base contact pad 120 may include a base contact surface 123 configured to be in communication with a board contact surface 127 of the board contact pad 125. In some embodiments, the base contact surface 123 and the board contact surface 127 are configured to correspond or match in terms of size, surface area and/or dimensions. For example, the base contact surface 123 and the board contact surface 127 may be configured to have corresponding surface size and/or shape.

At step 1260, the board contact pad 125 is attached or coupled to the base contact pad 120 using solder paste 165. As the coated active electrode board 150 is positioned for connecting to the base layer 103, the base contact surface 123 and the board contact surface 127 are aligned so that they may be connected, coupled or bounded using a solder paste.

Low temperature solder paste 165 can help ensure that the base contact surface 123 and the board contact surface 127 are bounded without burning the textile in the base layer 103.

At step 1270, the coated active electrode board 150 is attached to the base layer 103 using a laminate material 185.

In some embodiments, the laminate material 185 and the base layer 103 are bounded using heat activated glue.

In some embodiments, the laminate material 185 may include one or more Thermoplastic Polyurethane elastomers (TPU).

Laminate material 185 may be a non-conductive material. In some embodiments, the laminate material 185 may be stretch films made out of TPU. The laminate material 185, when used in small areas, are sufficiently thin and flexible as to not negatively affect fabric behavior of the textile in base layer 103.

In an embodiment, laminate material 185 is a TPU having resilient and flexible properties, and laminate material 185 may be configured to stretch when (textile) base layer 103 moves.

In some embodiments, the laminate material 185 and the base layer 103 can be bounded using heat activated glue. For example, laminate material 185 can be applied by first applying a glue to the surface area that will touch the base layer 103, then positioned in the desired area, facing down towards textile of the base layer 103, and then heat pressed to activate the glue.

In some embodiments, the glue may be chosen to be compatible with the material of the textile substrate in base layer 103. For example, the textile may be composed of: 69% nylon, 26% spandex, and 5% other.

An electrode according to the disclose herein may be used for different applications such that similar filament can be used in electrodes for bio-signal monitoring, functional electrical stimulation, heat generation, motion sensing, moisture sensing, respiration sensing, etc. Further, a single strand of the extruded filament may be knitted as an electrode such that material consumption may be reduced compared with other conductive filaments, e.g. carbon-contained nylon, silver plated nylon, etc. In some examples, because an extruded filament according to the disclosure herein may comprise silicone and/or rubber, an electrode made from the extruded element may have more grip when in contact with skin which may decrease motion artifact and retrieve bio-signals with higher resolution. In another example, electrodes according to the disclosure herein are biocompatible and such that they may be in contact with a human body for long-term monitoring and medical applications.

The electrode and/or conductive TPE disclosed herein may also be used for strain gauge. In an embodiment, the resistance of a filament according to the disclose herein may change by stretching, causing the distance between conductive particles in filament matrix to change; in turn, causing resistance to change. By measuring the change in resistance as the electrode, the electrode and/or filament may be used for stretch/motion sensing.

The electrode and/or conductive TPE disclosed herein may also be used for in heat applications. In an example, the conductive fillers, e.g. carbon-based fillers, may create high resistance so filament formed from conductive TPE polymer, or a sheet of the conductive TPE polymer, it can be used as a heating element by running an electric current through it. High conductivity yarns/filaments may be used as a bus and the extruded filament/sheet as heating element—due to the high resistance of sheet/filament, it will heat up and can be used in heat applications.

The electrode and conductive TPE disclosed herein may also be used as a moisture sensor. The polymer matrix may be selected such that it's sensitive to a group of solvents and it swells once it comes in contact with those types of solvents/solutions therefore the distance between its conductive particles will change so its resistance will change and it can be sensitive to moisture.

In some embodiments, as shown in FIGS. 25A to FIG. 28, an active electrode board 105 is mechanically joined with the base layer 103 and conductive pads using a mechanical pressing apparatus, which can include a top portion 2510 and a bottom portion 2540.

Figure 25A:
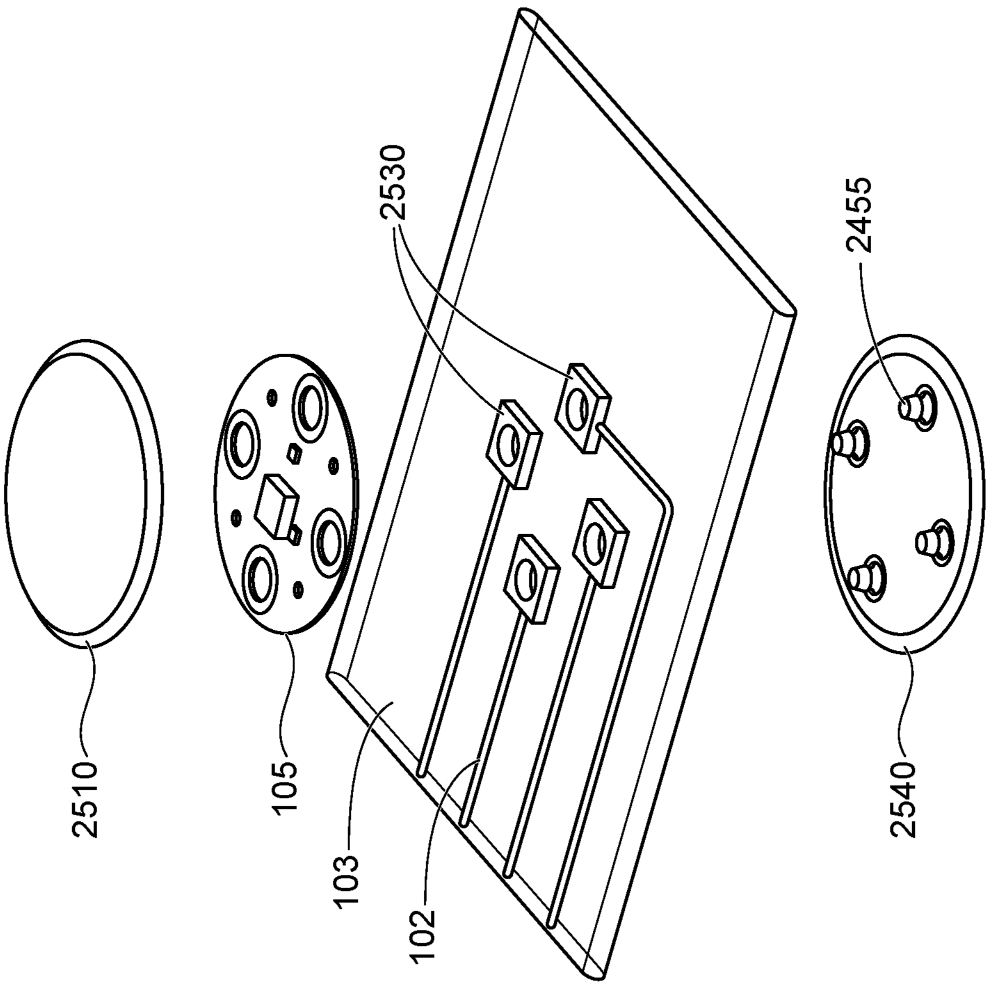
FIG. 25A shows an exploded view, from the top, of an example active electrode board mechanically joined with a base layer.

FIG. 25A shows an exploded view, from the top, of an example active electrode board 105 mechanically joined with a base layer.

Figure 25B:
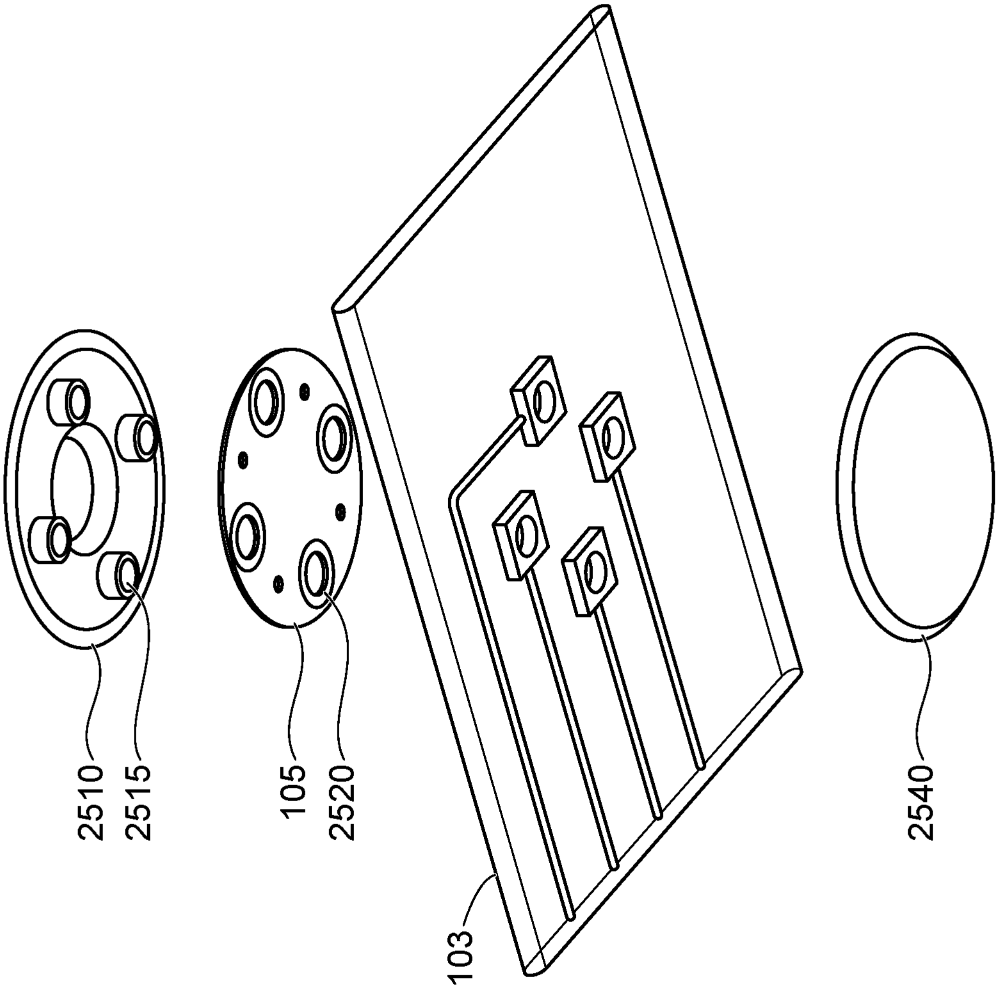
FIG. 25B shows an exploded view, from the bottom, of the example active electrode board mechanically joined with the base layer in FIG. 25A.

FIG. 25B shows an exploded view, from the bottom, of the example active electrode board mechanically joined with the base layer in FIG. 25A.

The active electrode board 105 and the base layer 103 may be placed (e.g., "sandwiched") between the top portion 2510 and the bottom portion 2540, with the two portions 2510, 2540 fused together through ultrasonic vibrations.

The base layer 103 may be a knit textile as described in this disclosure, containing one or more conductive layers (e.g., traces) 102 and one or more contact pads for communicating signals to and from the active electrode board 105. The conductive layers 102 may be made of silver, such as silver-plated nylon, polyester, Kevlar yarn and/or silver-plated copper microwire wrapped around polyester or nylon yarn.

Figure 26A:
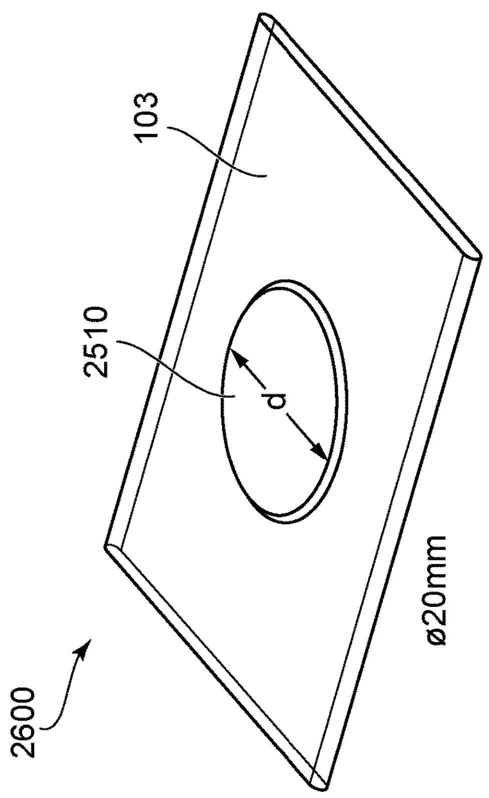
FIG. 26A shows a top view 2600 of the top portion 2510 mechanically joined with the base layer 103 in FIG. 25A.
Figure 26B:
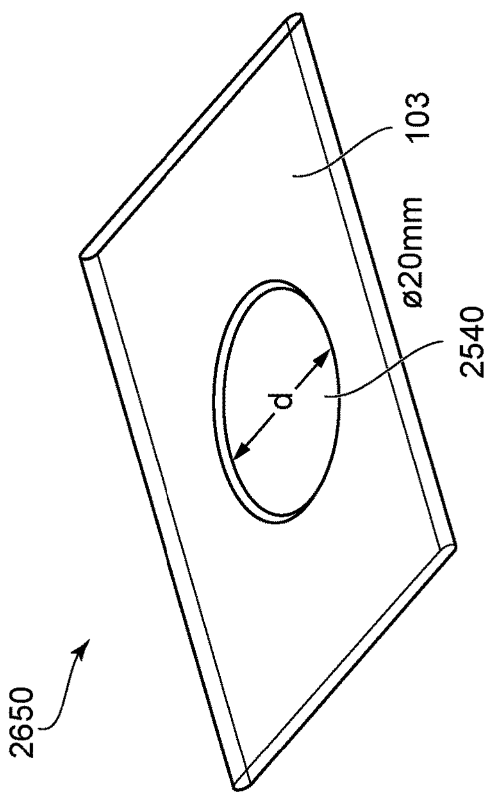
FIG. 26B shows a bottom view 2650 of the bottom portion 2540 mechanically joined with the base layer 103.

The two portions 2510, 2540 each has a rigid form, such as hard shell casing, for example, to protect the active electrode board 105 and to secure the active electrode board 105 firmly onto the base layer 103. The two portions 2510, 2540 may be made of thermoplastic material. FIG. 26A shows a top view 2600 of the top portion 2510 mechanically joined with the base layer 103 in FIG. 25A. FIG. 26B shows a bottom view 2650 of the bottom portion 2540 mechanically joined with the base layer 103. In some embodiments, the two portions 2510, 2540 may have identical shape, for example, they may each be a round hard shell object or casing having a diameter of 20 mm. In other embodiments, the two portions 2510, 2540 may have a different shape or form, long as they can be mechanically pressed or fused together to form a sealingly engagement.

In some embodiments, the two portions 2510, 2540 may contain appropriate mating engagement to be mechanically pressed or fused together to sealingly engage the board 105 with the base layer 103 as shown in FIGS. 25A, 25B, 26A and 26B.

Figure 27:
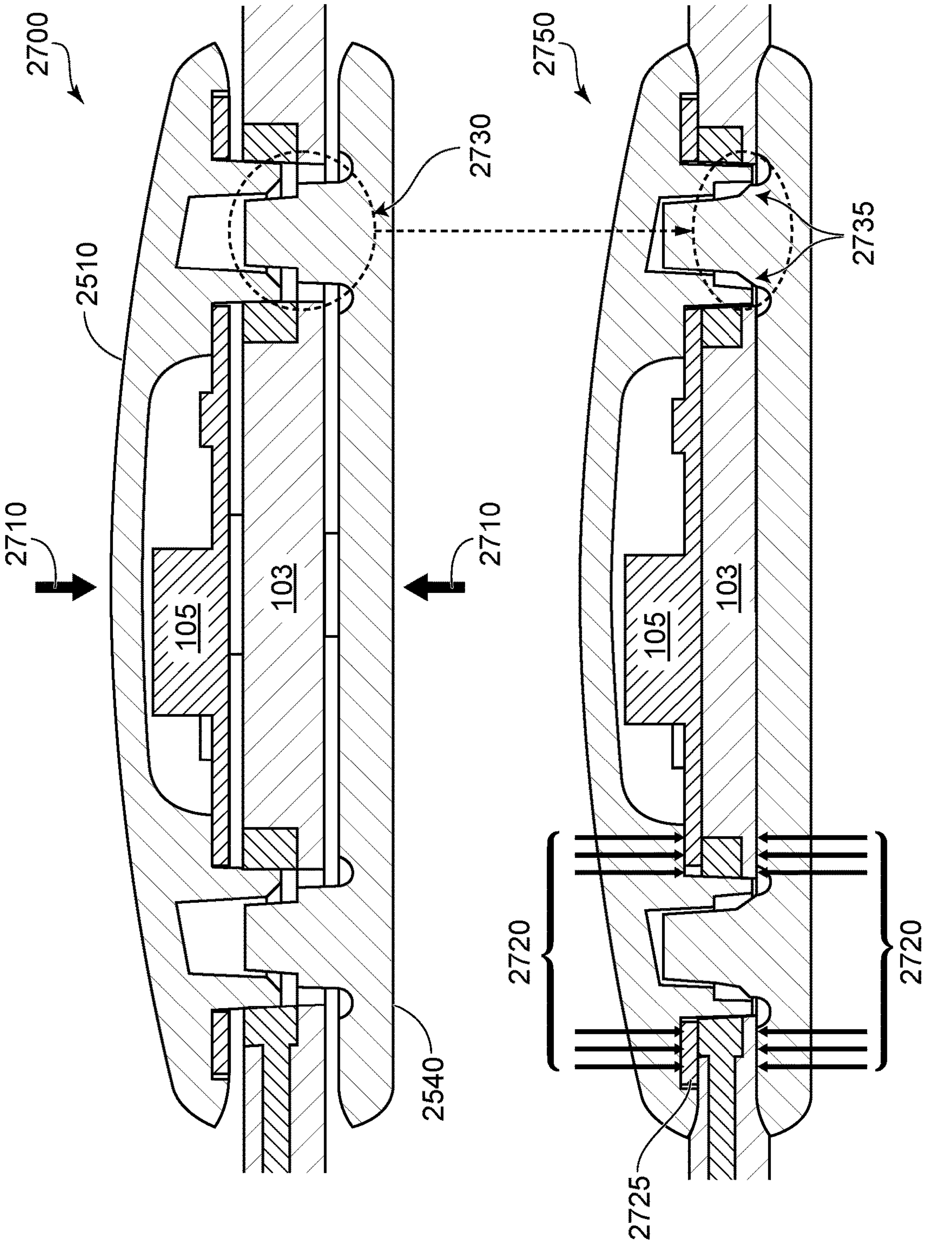
FIG. 27 shows a cross-sectional view of an example active electrode board in the process of being mechanically joined with a base layer using ultrasonic vibration, and a cross-sectional view of the example active electrode board and the base layer after being mechanically joined together using ultrasonic vibration.
Figure 28:
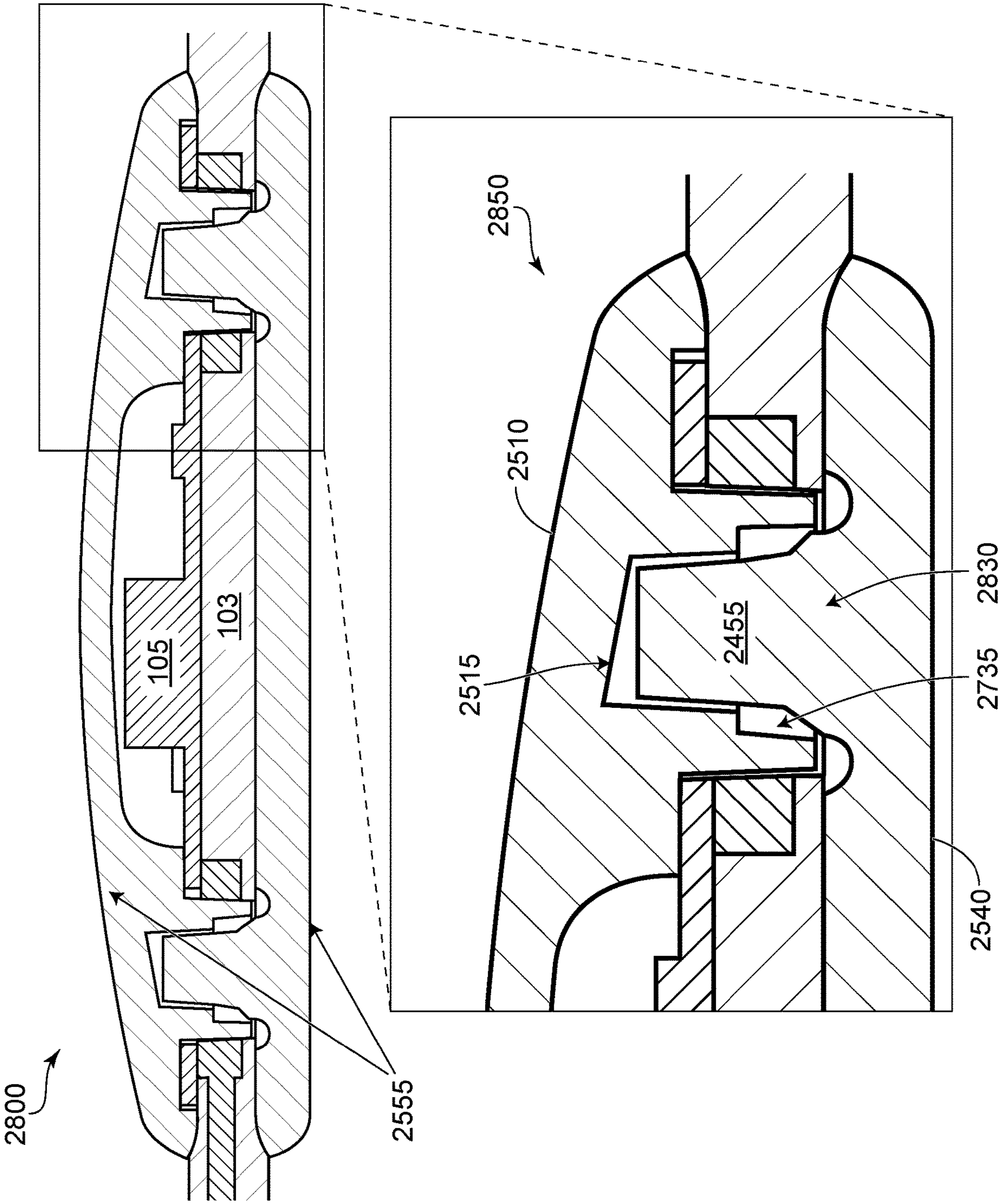
FIG. 28 shows another cross-sectional view of the example active electrode board after being mechanically joined with the base layer in FIG. 27.

For example, referring back to FIGS. 25A and 25B, the top portion 2510 may contain a plurality of receptacles 2515, and the bottom portion 2540 may contain a plurality of corresponding posts 2455, the receptacles 2515 of the top portion 2510 and the plurality of posts 2455 of the bottom portion 2540 may be mechanically fused together, for instance through ultrasonic welding or vibrations, to form a pressing fit or interference fit, such that a pair of receptacle 2515 and a corresponding post 2455 may, with mechanically pressing or fusing, form a seamless seal, as further shown in FIGS. 27 and 28.

In an example process of mechanically fusing the two portions 2510, 2540 together to connect the active electrode board 105 with the base layer 103, the active electrode board 105 is first placed within the top portion 2510. As shown in FIG. 25B, the active electrode board 105 contains a plurality of openings 2520, each for receiving a corresponding receptacle 2515 of the top portion 2510, so that the active electrode board 105 is securely placed within the top portion 2510.

Next, the bottom portion 2540 is placed through the base layer 103, with the base layer 103 on top of the bottom portion 2540. The base layer 103 contains a plurality of openings 2530, each receiving a corresponding post 2455 of the bottom portion 2540.

Then, the top portion 2510 securely containing the active electrode board 105 is placed on top of the base layer 103, corresponding to the bottom portion 2540. Each receptacle 2515 of the top portion 2510 and a corresponding post 2455 of the bottom portion 2540 are placed through a corresponding opening 2520 of the active electrode board 105 and a corresponding opening 2530 of the base layer 103, with the corresponding post 2455 of the bottom portion 2540 engaged within said receptacle 2515 of the top portion 2510.

Once the top portion 2510, the active electrode board 105, the base layer 103 and the bottom portion 2540 are placed in a correct position, they may be fused together using ultrasonic welding or vibration. FIG. 27 shows a cross-sectional view 2700 of an example active electrode board 105 being mechanically joined with a base layer 103 using ultrasonic vibration.

As shown in the cross-sectional view 2700, an ultrasonic welder device (not shown) may, during operation of ultrasonic welding, apply force 2710 from both a top direction (as applied to the top portion 2510) and a bottom direction (as applied to the bottom portion 2540) to mechanically fuse the top portion 2510, the active electrode board 105, the base layer 103 and the bottom portion 2540 together. The process of ultrasonic welding causes the contacting surfaces of the top portion 2510 and the bottom portion 2540 to melt and fuse together, forming a secure seal without leaks.

As shown in the cross-sectional views 2700 and 2750, the contacting surfaces of the top portion 2510 includes a small surface area on each receptacle 2515, and the corresponding contacting surfaces of the bottom portion 2540 is a small surface area on the corresponding receptacle post 2455 of the bottom portion 2540, as shown in circled area 2730.

In some embodiments, the receptacles of the top portion 2510 and the posts of the bottom portion 2540 may be manufactured to provide a shear joint for ultrasonic welding, which provides an interference fit for high-strength hermetic seals. During the welding operation, each pair of contacting surfaces of said receptacles and posts continue to melt along a vertical wall, forming a weld 2735 hidden between surfaces of the top portion 2510 and the bottom portion 2540.

After the ultrasonic welding operation, the base layer 103 is compressed, by forces 2720 from tightly sealed top portion 2510 and bottom portion 2540, against the contact pads 2725 on the underside of the active electrode board 105 to make electrical connection.

FIG. 28 shows another cross-sectional view 2800 of the example active electrode board 105 after being mechanically joined with the base layer 103. An example height of the entire device may be between 3 to 5 mm thick, such as e.g., 4.2 mm thick. The top portion 2510 and the bottom portion 2540 each has smooth surfaces 2555 both inside (potentially touching human skin) and outside. In an enlarged view 2850 of the welded area, it can be seen that the welds 2735 are hidden between surfaces of the top portion 2510 and the bottom portion 2540.

Figure 29:
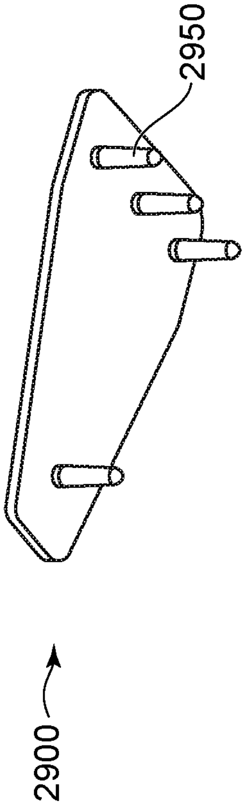
FIG. 29 shows an example plastic dome that can be integrated into the base layer to shield active electronic board.
Figure 29:
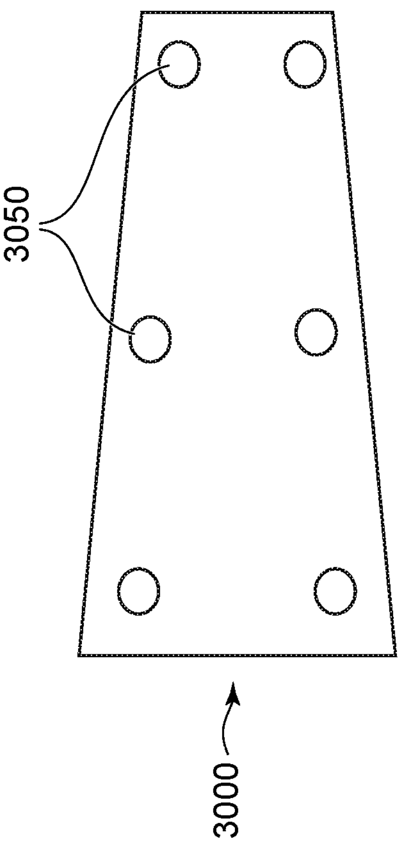
Figure 30:
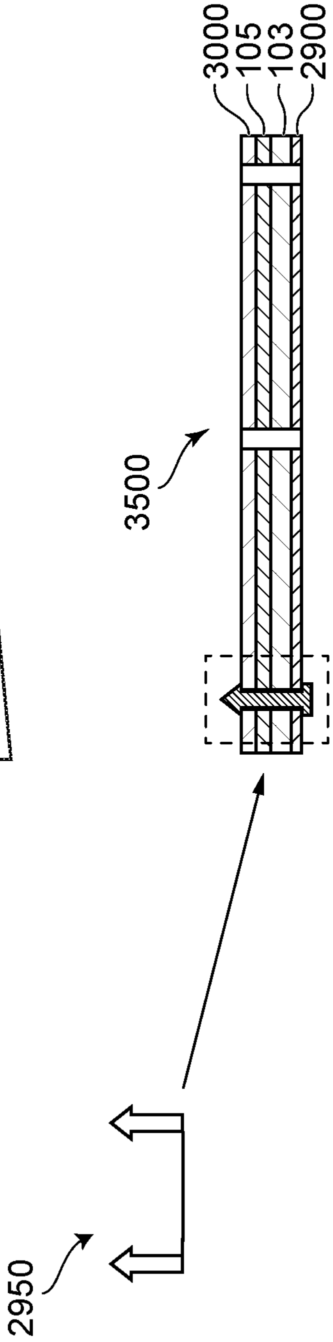
FIG. 30 shows a simplified cross-sectional view of the active electrodes being shielded by the plastic dome in FIG. 29.

FIGS. 29 and 30 show example embodiments in which the active electronic board 105 is mechanically pressed onto the base layer 103 using a plastic dome 2900.

FIG. 29 shows an example plastic dome 2900 that can be integrated into the base layer 103 to shield or protect the active electronic board 105. FIG. 30 shows a simplified cross-sectional view 3500 of the active electronic board 105 being shielded by the plastic dome 2900 in FIG. 29. A first film layer 3000, which may include a plurality of openings 3050, can be placed on top of the active electrode board 105. A second film layer 2900, which may include a plurality of conductive pins 2950, may be placed beneath the base layer 103. The conductive pins 2950 may act as heat steaks in order to facilitate the electrical connection between the base layer 103 and the board 105. Each conductive pin 2950 may be received by a corresponding opening 3050 of the first film layer 3000.

The plastic dome 2900 can be integrated into the base layer 103 by fusing material chemically compatible with the fabric or textile in the base layer 103. In some embodiments, the material is terminally and chemically compatible with the textile in the base layer 103.

A plastic dome 2900 may include electrically conductive pins 2950, which facilitates connections within a multilayer structure and promotes electrical current transmissions in desired areas. For example, the plastic dome 2900 can be manufactured using low melt material (e.g. PLA, ABS, or low melt PCL) or Nylon to have material compatibility with textile in base layer 103. The textile in base layer 103 may have, for example, a melting point about 265 degree Celsius.

The plastic dome 2900 can be manufactured using additive manufacturing and a combination of materials to generate various functional structures, such as a Fahrenheit cage structure to block electromagnetic fields.

The above description is meant to be exemplary only, and one skilled in the relevant arts will recognize that changes may be made to the embodiments described without departing from the scope of the invention disclosed. The present disclosure may be embodied in other specific forms without departing from the subject matter of the claims. The present disclosure is intended to cover and embrace all suitable changes in technology. Modifications which fall within the scope of the present invention will be apparent to those skilled in the art, in light of a review of this disclosure, and such modifications are intended to fail within the appended claims. Also, the scope of the claims should not be limited by the preferred embodiments set forth in the examples, but should be given the broadest interpretation consistent with the description as a whole.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus comprising:

a textile base layer integrated with an article of clothing;

a conductive layer in communication with a base contact pad mounted on the base layer;

an active electrode board in electrical communication with the base contact pad, the active electrode board configured to receive or send electrical signals from the base contact pad;

a coating on the active electrode board to provide a coated active electrode board;

a laminate material, wherein the coated active electrode board is attached to the base layer using the laminate material; and a contact layer comprising an electrode knitted from a filament comprising a thermoplastic elastomer blended with a conductive filler, the contact layer in electrical communication with the conductive layer, and the conductive layer is mounted on the base layer;

wherein the active electrode board comprises a board contact pad configured to receive or send electrical signals from the base contact pad; and wherein the base contact pad comprises a base contact surface configured to be in communication with a board contact surface of the board contact pad, and wherein the base contact surface and the board contact surface have corresponding surface size.

2. The apparatus of claim 1, wherein the contact layer comprises yarn comprising the filament, the filament comprising the conductive filler.

3. The apparatus of claim 1, wherein the conductive layer comprises silver yarn.

4. The apparatus of claim 1, wherein the base contact pad comprises conductive knitted yarn.

5. The apparatus of claim 4, wherein the conductive knitted yarn comprises copper microwire.

6. The apparatus of claim 1, wherein the base contact surface and the board contact surface have corresponding surface shape.

7. The apparatus of claim 6, wherein the base contact surface and the board contact surface are configured to be connected using a solder paste.

8. The apparatus of claim 7, wherein the solder paste is applied at a low temperature within a range of 130 to 170 degrees Celsius.

9. The apparatus of claim 1, wherein the coating exposes the board contact surface of the board contact pad for connecting to the base contact pad.

10. The apparatus of claim 1, wherein the laminate material and the base layer are bounded using heat activated glue.

11. The apparatus of claim 1, wherein the contact layer comprises an electrode configured to convert ionic current at a skin-electrode interface to electrical signals when the electrode is coupled to a user.

12. The apparatus of claim 1, wherein the active electrode board is mechanically captured between a top portion and a bottom portion of a mechanical pressing apparatus and the top and bottom portions are ultrasonically welded together via mating receptacles and posts to form shear joints that compress the textile base layer against the board contact pad of the active electrode board to maintain electrical contact.

* * * * *